United States Patent [19]
van Reis

[11] Patent Number: 5,490,937
[45] Date of Patent: * Feb. 13, 1996

[54] TANGENTIAL FLOW FILTRATION PROCESS AND APPARATUS

[75] Inventor: Robert D. van Reis, Redwood City, Calif.

[73] Assignee: Genentech, Inc., South San Francisco, Calif.

[ * ] Notice: The portion of the term of this patent subsequent to Oct. 26, 2010, has been disclaimed.

[21] Appl. No.: 271,223

[22] Filed: Jul. 6, 1994

Related U.S. Application Data

[63] Continuation of Ser. No. 91,945, Jul. 15, 1993, abandoned, which is a continuation of Ser. No. 583,886, Sep. 17, 1990, Pat. No. 5,256,294.

[51] Int. Cl.$^6$ .................................................. B01D 61/22
[52] U.S. Cl. ........................ 210/637; 210/641; 210/651
[58] Field of Search .................................. 210/637, 641, 210/137, 321.65, 651, 109, 321.84

[56] References Cited

U.S. PATENT DOCUMENTS

| | | |
|---|---|---|
| 3,744,642 | 7/1973 | Scala et al. . |
| 4,105,547 | 8/1978 | Sandblom . |
| 4,191,182 | 3/1980 | Popvich et al. . |
| 4,276,172 | 6/1981 | Henne et al. . |
| 4,350,156 | 9/1982 | Makchesky et al. . |
| 4,420,398 | 12/1983 | Castino . |
| 4,435,289 | 3/1984 | Breslau et al. . |
| 4,654,265 | 3/1987 | Breslau . |
| 4,689,267 | 8/1987 | Takamizawa et al. . |
| 4,741,829 | 5/1988 | Takemura et al. . |
| 4,746,436 | 5/1988 | Kopp et al. . |
| 4,789,489 | 12/1988 | Di Leo et al. . |
| 4,802,942 | 2/1989 | Takemura et al. . |
| 4,828,705 | 5/1989 | Thakore et al. ............... 210/636 |
| 4,874,516 | 10/1989 | Kondo . |
| 4,879,040 | 11/1989 | Prince et al. . |
| 4,935,139 | 6/1990 | Davidson et al. . |
| 4,971,696 | 11/1990 | Abe et al. . |
| 5,256,294 | 10/1993 | van Reis .......................... 210/637 |

FOREIGN PATENT DOCUMENTS

| | | |
|---|---|---|
| 0069523 | 1/1983 | European Pat. Off. . |
| 0112510 | 7/1984 | European Pat. Off. . |
| 0220749 | 5/1987 | European Pat. Off. . |
| 2065129 | 6/1981 | United Kingdom . |
| 8704169 | 7/1987 | WIPO . |

OTHER PUBLICATIONS

Baeyer et al., J. Membr. Sci., 22: 297–315 (1985), Cascade Plasmapherasis with Online Membrane Regeneration: Laboratory and Clinical Studies.
Castino et al., Artificial Kidney, Artificial Liver, and Artificial Cells, Chang, ed., Pleneum Publishing Corp., N.Y., pp. 259–266, (1978), The Filtration from Whole Blood: A Novel Approch to Clinical Detoxification.
Chakrovorty et al., Desalination, 78(2):279–286 (1990), Concentration and Purification of Gelatin Liquor by Ultrafiltration.
Cheryan, Ultrafiltration Handbook, (Technomic Publ. Co., Inc., Pennsylvania, 1986) pp. 218–221, p. 311, Fractionation of Macromolecules.
Flachel et al., Advances in Biochemical Engineering/Biotechnology, 26:73–142, (Downstream Processing, 1983), "Ultrafiltration for the Separation of Biocatalysts."Gabler, ASM News, 50(7):299–304 (1984), Tnagential Flow Filtration for Processing Cells, Proteins, and Other Biological Components.

(List continued on next page.)

Primary Examiner—Frank Spear
Attorney, Agent, or Firm—Janet E. Hasak

[57] ABSTRACT

Processes and apparati are provided for separating species of interest from a mixture containing them which comprises subjecting the mixture to tangential-flow filtration, wherein the filtration membrane preferably has a pore size that retains species with a size up to about 10 microns, and the flux is maintained at a level ranging from about 5 % up to 100 % of transition point flux.

12 Claims, 11 Drawing Sheets

OTHER PUBLICATIONS

Michaels, Chem. Eng. Prog., 64(12):31–44 (1968), New Separation Technique for CPI.

Michaels, Chem. Tech., pp. 36–43 (Jan. 1981), Ultrafiltration: An Adolescent Technology.

Michaels, Polymer Science and Technology, vol. 13, Ultrafiltration Membraines and Applications, pp. 1–19, (Plenum Press, N.Y., 1979), "Fifteen Years of Ultrafiltration: Problems and Future Promises of an Adolescent Technology".

Michaels et al., Desalination, 53:231–258 (1985), Membranes in Biotechnology: State of the Art.

Millipore 1990 Catalog, p. 213, Militan High Resolution Tangential Flow (HRTF) System.

Nelson, Proceeding of the International Workshop on Technology for Protein Separation and Improvement of Blood Plasma Fractionation, Reston, Va., Sep. 7–9, 1977, pp. 133–137, Ultrafiltration in Plasma Fractionation.

Porter, ed., "Handbook of Industrial Membrane Technology", (Noyes Publ., Park Ridge, N.J., 1990) pp. 164–173.

Porter & Michaels, Chem. Tech., pp. 56–63 (Jan. 1971), Membrane Ultrafiltration.

Rautenbach et al., Chem.–Ing., Tech. 54(3), 229–240, (1982) Stoff.

van Reis et al., J. Interferon Res., 2(4):533–541 (1982), Production and Recovery of Human Leukocyte–Derived Alpha Interferon Using a Cascade Filtration System.

TANGENTIAL FLOW FILTRATION PROCESS AND APPARATUS

This is a continuation of serial No. 08/091,945 filed Jul. 15, 1993, now abandoned which is a continuation of Ser. No. 07/583,886 filed on 17 Sep. 1990, now U.S. Pat. No. 5,256,294.

BACKGROUND OF THE INVENTION

1. Field of the Invention

This invention relates to the purification and separation of moieties, particularly those of biological interest, from mixtures containing them utilizing improved tangential-flow filtration processes and apparati.

2. Description of Related Disclosures

Several methods are currently available to separate molecules of biological interest, such as proteins, from mixtures thereof. One important such technique is affinity chromatography, which separates on the basis of specific and selective binding of the desired molecules to an affinity matrix or gel. Affinity gels typically consist of a ligand-binding moiety immobilized on a gel support. For example, GB 2,178,742 utilizes affinity chromatography to purify hemoglobin and its chemically modified derivatives based on the fact that native (oxy)hemoglobin binds specifically to polyanionic moieties of certain affinity gels. In this process, unmodified hemoglobin is retained by the affinity gel, while modified hemoglobin, which cannot bind to the gel because its polyanion binding site is covalently occupied by the modifying agent, is eluted. Affinity chromatography columns are highly specific and thus yield very pure products; however, affinity chromatography is a relatively expensive process.

Another known separation method is membrane filtration, which separates dissolved and suspended solutes on the basis of their size. In the simplest form of this process, a solution is forced under pressure through a filter membrane with pores of a defined size. Solutes larger than the pore size of the membrane filter are retained, while smaller solutes are carried convectively through the membrane with the solvent.

Such membrane filtration processes generally fall within the categories of reverse osmosis, ultrafiltration, and microfiltration, depending on the pore size of the membrane. Conventionally, ultrafiltration employs membranes rated for retaining solutes between approximately 1 and 1000 kDa in molecular weight, reverse osmosis employs membranes capable of retaining salts and other low molecular weight solutes, and microfiltration, or microporous filtration, employs membranes in the 0.1 to 10 micrometer (micron) pore size range, typically used to retain colloids and microorganisms.

Over the past 25 years, ultrafiltration has progressed from a small-scale laboratory tool to a fully established unit operation capable of processing thousands of liters per hour. Ultrafiltration is widely used for protein concentration and removal of salts and alcohols, as well as in depyrogenation of process and rinse water, saline solutions, and low molecular weight additives. The advantages of ultrafiltration include low energy cost, low capital equipment outlay, and efficient and controllable operation with very low denaturation of product.

However, limitations exist on the degree of protein purification achievable in ultrafiltration. These limits are due mainly to the phenomena of concentration polarization, fouling, and wide membrane pore size distribution. Hence, solute discrimination is poor. See, e.g., Porter, ed., *Handbook Of Industrial Membrane Technology* (Noyes Publications, Park Ridge, N.J., 1990), pp. 164–173.

A polarized layer of solutes acts as an additional filter in series with the original ultrafilter, and provides significant resistance to the filtration of solvent. The degree of polarization increases with increasing concentration of retained solute in the feed, and can lead to a number of seemingly anomalous or unpredictable effects in real systems. For example, under highly polarized conditions, filtration rates may increase only slightly with increasing pressure, in contrast to unpolarized conditions, where filtration rates are usually linear with pressure. Use of a more open, higher-flux membrane may not increase the filtration rate, because the polarized layer is providing the limiting resistance to filtration. The situation is further complicated by interactions between retained and eluted solutes.

A result of concentration polarization and fouling processes is the inability to make effective use of the macromolecular fractionation capabilities of ultrafiltration membranes for the large-scale resolution of macromolecular mixtures such as blood plasma proteins See Michaels, "Fifteen Years of Ultrafiltration: Problems and Future Promises of an Adolescent Technology" in Anthony R. Cooper, ed., *Ultrafiltration Membranes and Applications, Polymer Science and Technology*, 13(Plenum Press, N.Y., 1979), pp. 1–19, at p. 9. Consequently, the potentially exciting utilization of membrane ultrafiltration for large-scale complex macromolecular mixture-separations currently performed by such techniques as gel permeation, adsorption, or ion-exchange chromatography, selective precipitation, or electrophoresis is considered elusive.

The merits of various multi-stage and cascaded cross-flow filtration schemes have been examined on paper, with a slightly improved effect. See Michaels and Matson, *Desalination*, 53: 231–258 (1985), p. 235 in particular. See also the experimental flow circuit in FIG. 1 on p. 535 of van Reis et al., *J. Interf. Res.*, 2: 533–541(1982), and M. Cheryan, *Ultrafiltration Handbook*, (Technomic Publishing Co., Inc.: Penn., 1986), p. 311, where a cascade membrane recycle bioreactor system for producing protein hydrolyzate fractions of different molecular sizes is described.

To circumvent the effects of concentration polarization, several processes have been developed that modify the feed plasma source to improve selectivity and flux (defined as the filtration rate divided by the membrane area). For example, UK Appln. No. 2,065,129 describes a separation technique wherein total serum is diluted to reduce total protein and salt concentration while the pH is adjusted to between 3.8 and 4.7 prior to ultrafiltration. Baeyer et al., *J. Membrane Sci.*, 22:297–315(1985) describes a process wherein the plasma is first diluted by a factor of 12 prior to ultrafiltration. U.S. Pat. No. 4,350,156 discloses a process for removing macromolecules from plasma by cooling the plasma to about 10° C. and then filtering the macromolecules from the cooled plasma to form a filtered low molecular weight plasma stream. This process does not employ an ultrafiltration membrane.

One major approach to address concentration polarization in ultrafiltration systems has been to control the fluid flow pattern so as to enhance transport of the retained solute away from the membrane surface and back into the bulk of the feed. In a process known as tangential-flow ultrafiltration (TFF), the feed stream is recirculated at high velocities tangential to the plane of the membrane to increase the mass-transfer coefficient for back diffusion. Gabler, *ASM*

*News*, 50:299(1984). The fluid flowing in a direction parallel to the filter membrane acts to clean the filter surface continuously and prevents clogging by non-filterable solutes. Another filtration device that achieves the same effects as TFF is a rotary filtration device containing an outer and inner cylinder, where the inner cylinder is rotated to create a vortex to obtain high velocity without a change in pressure.

In TFF, a pressure differential gradient, called transmembrane pressure (TMP), is applied along the length of the membrane to cause fluid and filterable solutes to flow through the filter. Flux is independent of TMP above a certain minimum value that can be determined empirically. To achieve maximum flux, ultrafiltration systems are typically run with an outlet pressure equal to or greater than this minimum value. Hence, flux is constant along the length of the membrane, while the TMP varies. Both laminar and turbulent flow approaches have been used with some success; however, conventional TFF still affords only poor molecular size resolution.

Attempts have been made to combine affinity separation with TFF to increase the ability of TFF to separate selectively based on biological differences. See WO 87/04169 published Jul. 16, 1987. In TFF ultrafiltration, a soluble affinity polymer is placed in the mixture containing the fractions to be separated, on the upstream side of the filter membrane. Since the polymer is much larger than the solute particles, a filter can be selected that will allow unbound solutes to pass through the filter but prevent the passage of polymer and any substance bound to the polymer. Due to the problems posed by conventional TFF, however, even this approach has met with limited success.

U.S. Pat. No. 4,105,547 issued Aug. 8, 1978 discloses a filtering process, designed especially for ultrafiltration, in which a filterable fluid is caused to flow under pressure through a filtering passage extending along one side of a filter, in such a way that a considerable pressure drop arises along the filter area in the flow direction. In the apparatus employed, the pressure difference between both sides of the filter is maintained substantially constant throughout the entire filter area. The patentees teach that clogging of the filter tending to reduce the flow can be compensated for by successively raising the driving pressure to a level that is below the pressure-independent region of the flux v. TMP curve. This raising of the driving pressure results in constant filtration rate, but not higher selectivity. In addition, the patentees disclose that the transmembrane pressure should be increased as the filtration is being carried out. Other features taught by the patentees include better membrane cleaning.

U.S. Pat. No. 4,191,182 issued Mar. 4, 1980 discloses in one embodiment a process and apparatus for continuously separating blood into plasma and cellular component fractions. The process involves withdrawing whole blood and pumping it into a filtering chamber of a filtration cell, and continuously filtering the whole blood by passing it in a flow over and parallel to a membrane of a certain pore size range and at a flow rate sufficient to provide a specified shear stress range at the membrane interface within particular TMP confines. Then, the cellular component fraction is continuously mixed with an amount of replacement fluid substantially equal to the separated plasma fraction, and the cellular component fraction and replacement fluid mixture are continuously returned to a blood vessel of the donor.

In one embodiment a portion of the plasma fraction separated from the whole blood is recycled in a flow parallel to and in the same direction as the flow of the whole blood over the filter membrane, but on the opposite side of the membrane from the flow of whole blood, to obtain a substantially uniform TMP across the entire length of the membrane. The purpose of this embodiment is to increase filtration rates to twice that when plasma filtrate is removed from the filtrate chamber without such recycling. Also, it allows for the use of long filtering chamber flow paths and for the design of coil-type filtration cells.

More recently, U.S. Pat. No. 4,789,482 issued Dec. 6, 1988 describes a process for separating blood plasma into high and low molecular weight streams. The blood plasma is introduced at a certain shear rate into an inlet portion of a separation unit containing several thin channels or hollow fibers with walls through which ultrafiltration is carried out. The high and low molecular weight streams are separated from the unit, the high molecular weight stream is recirculated to an inlet portion of the separation unit to form a recirculation stream, and the ratio of the recirculation stream flow rate to the permeate stream flow rate is controlled between 5 and 100, with the ratio of TMP at outlet to inlet of the separation unit between about 0 and 0.85. This method uses the conventional thinking regarding ultrafiltration, i.e., that the outlet and inlet TMPs must be different; thus, it does not overcome the concentration polarization problem inherent in ultrafiltration.

Despite all of these attempts at improvement, it is still the case that although concentration polarization can be modified, and quite high filtration rates can be achieved even from very concentrated solutions if appropriate flow conditions are supplied, the polarized layer can never be completely eliminated. This is observed from a number of protein mixtures, and a rule of thumb has evolved that fractionation of protein mixtures by simple ultrafiltration will probably be highly inefficient unless the species are at least a factor of ten different in molecular weight. Although some closer separations have been occasionally reported, they have always been under extremely and impractically dilute conditions. Nelsen, "Ultrafiltration in Plasma Fractionation", in *Proceedings of the Internat. Workshop on Technology for Protein Separation and Improvement of Blood Plasma Fractionation*, Reston Va., Sep. 7–9, 1977, Sandberg, ed., NIH, DHEW Pub. No. NIH 78–1422, p. 137; Flaschel et al, "Ultrafiltration for the Separation of Biocatalysts", in Fiechter, ed., *Advances in Biochemical Engineering/Biotechnology*, Vol. 26(Downstream Processing), pp. 73–142 (1983), particularly, p. 124; Cheryan, supra, p. 218–219.

It is an object of the present invention to provide tangential-flow filtration processes for separating species such as particles and molecules by size, which processes are selective for the species of interest, resulting in higher-fold purification thereof.

It is another object to provide improved filtration processes, including ultrafiltration processes, for separating biological macromolecules such as proteins which processes minimize concentration polarization and do not increase flux.

It is another object to provide a filtration process that can separate by size species that are less than ten-fold different in size and does not require dilution of the mixture prior to filtration.

These and other objects will become apparent to those skilled in the art.

SUMMARY OF THE INVENTION

These objects are achieved in a process for separating species of interest from a mixture, which process comprises filtering the mixture by tangential-flow filtration through a membrane having a pore size that separates the species of interest from the mixture, while maintaining flux at a level ranging from about 5 to 100% of transition point flux.

Preferably, transmembrane pressure for the filtration is maintained substantially constant along the membrane at a level no greater than the transmembrane pressure at the transition point of the filtration.

In a more specific aspect, the species of interest has a size of up to about 10 microns. In an even more specific aspect, this invention provides a process for separating species of interest having a molecular weight of about 1 to 1000 kDa from a mixture which process comprises filtering the mixture by tangential-flow filtration through a filtration membrane having a pore size that separates said species of interest from the mixture, while maintaining flux at a level ranging from about 5 to 100% of transition point flux, whereby the species of interest are selectively separated from the mixture.

In yet another aspect, this invention provides a process for separating species of interest having a size of about 0.1 to 10 microns from a mixture which process comprises filtering the mixture by tangential-flow filtration through a filtration membrane having a pore size that separates said species of interest from the mixture, while maintaining flux at a level ranging from about 5 to 100% of transition point flux, whereby the species of interest are selectively separated from the mixture.

In a still further aspect, this invention supplies a tangential-flow filtration apparatus comprising:

(a) a vessel in fluid communication with a filtration unit comprising a plurality of adjacent, parallel filtration membranes having the same pore size, which separate said unit into a filtering and filtrate chamber, said filtering and filtrate chambers each having an inlet and an outlet, (b) means connecting an inlet of the filtering chamber to the vessel, which contains means for pumping fluid from the vessel to the inlet of said filtering chamber, (c) means for generating a pressure gradient within the filtrate chamber, and (d) means for collecting filtrate from the outlet of said filtrate chamber.

Preferably, the membrane pores range in size from 1 kDa to 10 microns. Also preferably, the generating means is a means for recirculating filtrate through the filtrate chamber parallel to the direction of the fluid in the filtering chamber, and more preferably a pump.

In yet another aspect, this invention provides a tangential-flow filtration apparatus comprising a filtration unit having a plurality of layered filtering and filtrate chambers, all but the last filtrate chamber in the layering order having inlet and outlet means each in fluid communication with a separate vessel, and the last filtrate chamber having an outlet means for circulating filtrate to the vessel that is in fluid communication with the first filtering chamber in the layering order, each chamber having a means for pumping fluid from the vessel to the inlet means of the chamber, and each chamber being separated from its adjacent chamber by a filtration membrane, the apparatus being such that the flow of fluid from the inlet to the outlet means of all chambers is parallel and in the same direction, the first filtration membrane in the layering order has a pore size that retains species of the largest size, the last filtration membrane in the layering order has a pore size that retains species of the least size, and the middle filtration membrane(s) in the layering order have a pore size that retains species of sizes in descending order from the first to the last of the middle layered membrane(s).

In a still further aspect, the invention provides a tangential-flow filtration apparatus comprising:

(a) a first vessel in fluid communication with a first filtration unit having a first filtration membrane that separates said unit into a first filtering and filtrate chamber, said filtering and filtrate chambers each having an inlet and an outlet, (b) means connecting an inlet of the first filtering chamber to the first vessel, which contains means for pumping fluid from the first vessel to the inlet of the first filtering chamber, (c) means for generating a pressure gradient within the first filtrate chamber, (d) a second vessel in fluid communication with a second filtration unit having a second filtration membrane that separates said unit into a second filtering and filtrate chamber, said filtering and filtrate chambers each having an inlet and an outlet, (e) means for circulating the filtrate from the outlet of the first filtrate chamber to the second vessel, (f) means connecting an inlet of the second filtering chamber to the second vessel, which contains means for pumping fluid from the second vessel to the inlet of the second filtering chamber, (g) means for generating a pressure gradient within the second filtrate chamber, (h) a third vessel in fluid communication with a third filtration unit having a third filtration membrane that separates said unit into a third filtering and filtrate chamber, said filtering and filtrate chambers each having an inlet and an outlet, (i) means for circulating the filtrate from the outlet of the second filtrate chamber to the third vessel, (j) means connecting an inlet of the third filtering chamber to the third vessel, which contains means for pumping fluid from the third vessel to the inlet of the third filtering chamber, and (k) means for circulating the filtrate from the outlet of the third filtrate chamber to the first vessel, wherein the first filtration membrane has a pore size that retains species of the largest size, the second filtration membrane retains species of a size intermediate to the pore size of the first and third filtration membranes, and the third filtration membrane has a pore size that retains species of the smallest size.

Optionally, the lattermost apparatus also contains means for generating a pressure gradient within the third filtrate chamber. Preferably, all the generating means are means for recirculating filtrate through the filtrate chamber parallel to the direction of the fluid in the filtering chamber.

Also, preferably all the membranes of this latter apparatus are ultrafiltration membranes of decreasing pore size in the cascade.

Much of the literature to date operates under the assumption that size separation must take place in the pressure-independent region of the curve of flux versus TMP. The size separation of this invention is achieved by operation of the tangential-flow filtration in the pressure-dependent region of the flux versus TMP curve. In general, the flux is actually decreased in the process of this invention relative to the rate obtained when filtration is carried out in the pressure-independent region of the flux versus TMP curve. Further, the filtration is carried out such that the TMP is approximately constant with time or decreases throughout the filtration.

The maintenance of the TMP within this pressure-dependent region results in a dramatic decrease in retention of molecules with molecular weights lower than the membrane rating. In addition, this feature greatly improves the overall selectivity of the system for the species desired to be purified, thereby overcoming the barrier of the concentration polarization layer. Hence, a greater fold purification of the species of interest is obtained over conventional tangential-flow filtration, where flux D is greater than about 100% of transition point flux. An additional advantage of the process resides in separating species that are less than ten times smaller in molecular weight than the larger species of the mixture.

All of these desirable attributes are accomplished without the need to raise the driving pressure to a level just below the level above which the filtrate flow is independent of the driving pressure. These features are also achieved without the need to dilute the mixture before filtration. Thus, the process can be carried out for the concentration level of the protein at the stage of the process where the TFF step is introduced, avoiding a deliberate dilution of the protein concentration at that stage.

DETAILED DESCRIPTION OF THE PREFERRED EMBODIMENTS

A. Definitions

Figure 1A:
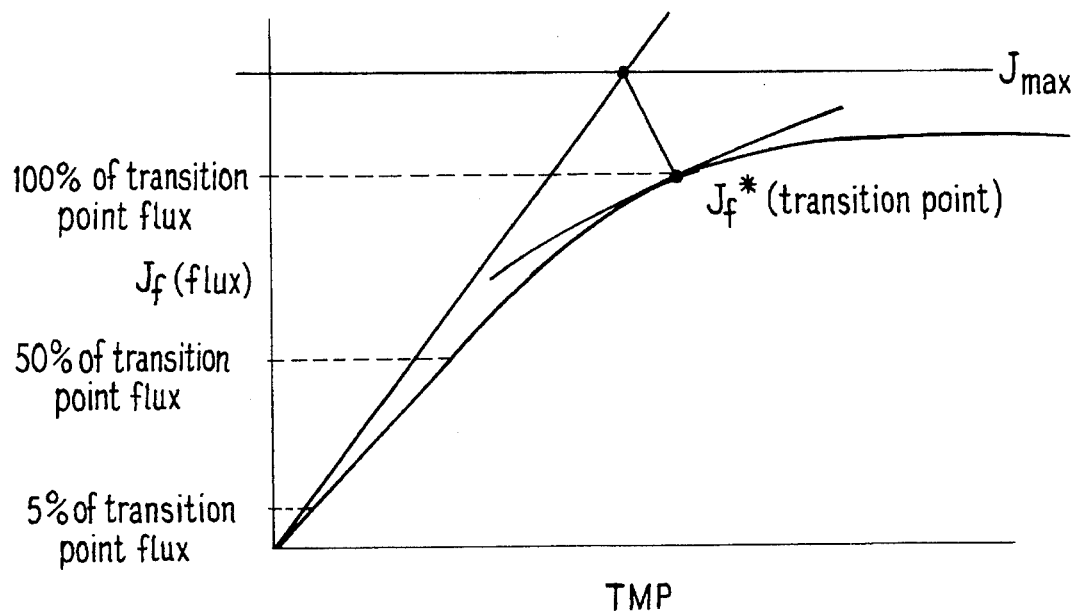
FIG. 1A depicts a graph of flux ($J_f$) versus TMP for tangential-flow filtration using a single membrane. On this graph the range of 5 to 100% of transition point flux is indicated, as well as the transition point ($J_{f*}$) and the lines and curves used to determine transition point, defined further below.

The term "species" as used herein generally means particles or molecules that are to be separated from a solution or suspension in a fluid, e.g., a liquid. The particles or molecules are separated from the fluid and, in most instances, from other particles or molecules in the fluid. The size of the species of interest to be separated will determine the pore size of the membrane to be utilized. Preferably, the species are biological entities of natural biological or biochemical origin or produced by biological or biochemical processes. Examples of preferred species include mammalian cells and microorganisms such as bacteria, fungi, and yeast (both cells and microorganisms being amenable to microfiltration techniques), as well as species of suitable size for ultrafiltration, including polypeptides, proteins, cellular components, DNA, colloids, mycoplasm, endotoxins, viruses, carbohydrates, and other molecules of biological interest, whether glycosylated or not.

The species of interest for ultrafiltration preferably are biological macromolecules having a molecular weight of at least about 1000 daltons, and most preferably polypeptides and proteins. Also preferred is that the species of interest be less than tenfold larger than the species from which it is to be separated, i.e., contaminant, or be less than ten-fold smaller than the species from which it is to be separated.

As used herein, the term "tangential-flow filtration" refers to a process in which the fluid mixture containing the components to be separated by filtration is recirculated at high velocities tangential to the plane of the membrane to increase the mass-transfer coefficient for back diffusion. In such filtrations a pressure differential is applied along the length of the membrane to cause the fluid and filterable solutes to flow through the filter. This filtration is suitably conducted as a batch process as well as a continuous-flow process. For example, the solution may be passed repeatedly over the membrane while that fluid which passes through the filter is continually drawn off into a separate unit or the solution is passed once over the membrane and the fluid passing through the filter is continually processed downstream.

As used herein, the term "ultrafiltration" is used for processes employing membranes rated for retaining solutes having a molecular weight between about 1 kDa and 1000 kDa.

As used herein, the term "reverse osmosis" refers to processes employing membranes capable of retaining solutes of a molecular weight less than 1 kDa such as salts and other low molecular weight solutes.

As used herein, the term "microfiltration" refers to processes employing membranes in the 0.1 to 10 micron pore size range.

As used herein, the expression "transmembrane pressure" or "TMP" refers to the pressure differential gradient that is applied along the length of a filtration membrane to cause fluid and filterable solutes to flow through the filter.

As used herein, the expression "substantially constant" as applied to TMP refers to a TMP that does not increase or decrease along the length of the membrane generally by more than about 10 psi of the average TMP, and preferably by more than about 5 psi. As to the level of the TMP throughout the filtration, the TMP is held constant or is lowered during the concentration step to retain selectivity at higher concentrations. Thus, "substantially constant TMP" refers to TMP versus membrane length, not versus filtration time.

As used herein, the expression "same pore size" as applied to the filtration membrane refers to membranes that are rated or sold as having the same pore size, even though the actual pore sizes of the membranes vary somewhat.

As used herein, the expression "adjacent" as describing filtration membranes means substantially adjacent in that the membranes may be physically layered on top of one another or with a slight space between.

As used herein, the expression "means for generating a pressure gradient within the filtrate chamber" refers to a mechanism for creating a gradient in pressure so that the transmembrane pressure can be operated substantially at a constant level in the pressure-dependent region of the flux versus TMP curve.

As used herein, the expression "means for recirculating filtrate through the filtrate chamber parallel to the direction of the fluid in the filtering chamber" refers to a mechanism or configuration that directs a portion of the fluid from the filtrate chambers to flow parallel to and in substantially the same direction (allowing for some eddies in flow to occur) as the flow of fluid passing through the adjacent filtering chamber from the inlet to the outlet of the filtering chamber. Preferably, this means is a pumping means.

As used herein, the expression "vessel" refers to a container or tank for storing, dispensing, and/or receiving fluid.

As used herein, the expression "transition point" refers to a fixed point on a curve of flux versus TMP that is determined as follows: Experimental data of flux ($J_f$) versus TMP are collected in either a short-path-length module where the inlet and outlet TMP are ±10% of each other, or in a full-path-length module where the same conditions are met by using recirculating filtrate. The experimental data are fit to the curve defined by the equation:

$$J_f = J_{max} \times TMP/(k+TMP), \text{ (Equation 1)}$$

where $J_{max}$ (an asymptotic value) and k are determined by linear regression of $1/J_f$ versus $1/TMP$, which yields an intercept of $1/J_{max}$ and a slope of $k/J_{max}$. Referring to FIG. 1A, graphically the transition point is defined by the following criteria: Determine the intercept of $J_f=J_{max}$ and the tangent through the origin to the curve defined by equation 1 (the tangent is $J_f=J_{max} \times TMP/k$). A line is then drawn through that intercept and perpendicular to a tangent on the above curve. The intercept of this latter line and the curve defines the transition point flux. Mathematically, this transition point ($j_f^*$) is defined as the real solution in the experimental data range to the following equation:

$$(J_{max} \times J_f^*)^4 = J_{max} - k^2(J_{max} - 2J_f^*) \text{ . (Equation 2)}$$

B. Modes for Carrying Out the Invention

Figure 1B:
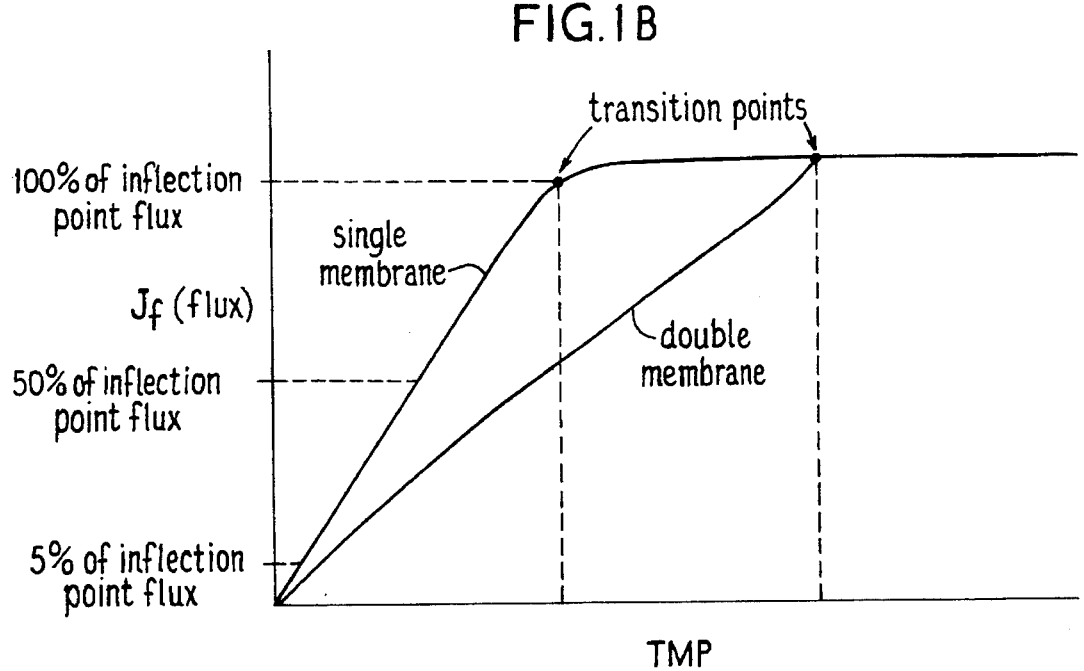
Figure 1B shows the transition points for single and double membranes.

In its broadest aspect, the high-performance tangential-flow filtration process contemplated herein involves passing the mixture of the species to be separated through one or more filtration membranes in an apparatus or module designed for a type of tangential-flow filtration under certain conditions of TMP and flux. The TMP is held at a range in the pressure-dependent region of the flux v. TMP curve, namely, at a range that is no greater than the TMP value at the transition point. Thus, the filtration is operated at a flux ranging from about 5% up to 100% of transition point flux. See FIGS. 1A and 1B, wherein the flux v. TMP curve is depicted along with the transition point. As a result, the species of interest are selectively retained by the membrane as the retentate while the smaller species pass through the membrane as the filtrate, or the species of interest pass through the membrane as the filtrate and the contaminants in the mixture are retained by the membrane.

It is noted that the TMP does not increase with filtration time and is not necessarily held constant throughout the filtration. The TMP may be held approximately constant with time or may decrease as the filtration progresses. If the retained species are being concentrated, then it is preferred to decrease the TMP over the course of the concentration step.

Each membrane preferably has a pore size that retains species with a size of up to about 10 microns, more preferably 1 kDa to 10 microns. Examples of species that can be separated by ultrafiltration include proteins, polypeptides, colloids, mycoplasm, endotoxins, viruses, amino acids, DNA, RNA, and carbohydrates. Examples of species that can be separated by microfiltration include mammalian cells and microorganisms such as bacteria.

Because membrane filters are not perfect and may have holes that allow some intended retentate molecules to slip through, a preferred aspect herein is to utilize more than one membrane having the same pore size, where the membranes are placed so as to be layered parallel to each other, preferably one on top of the other. Preferably the number of membranes for this purpose is two.

While the flux at which the pressure is maintained in the above process suitably ranges from about 5 to 100%, the lower the flux, the larger the surface area of the membrane required. Thus, to minimize membrane cost, it is preferred to operate at a pressure so that the flux is at the higher end of the spectrum. The preferred range is from about 50 to 100%, and the more preferred range is about 75 to 100%, of the transition point flux.

While the TMP need not be maintained substantially constant along the membrane surface, it is preferred to maintain the TMP substantially constant. Such a condition is generally achieved by creating a pressure gradient on the filtrate side of the membrane. Thus, the filtrate is recycled through the filtrate compartment of the filtration device in the same direction and parallel to the flow of the mixture in the retentate compartment of the device. The inlet and outlet pressures of the recycled material are regulated such that the pressure drop across the filtrate compartment equals the pressure drop across the retentate compartment.

Several practical means can be used to achieve this filtrate pressure gradient. One example is the configuration shown in FIG. 2A. Thus, the mixture to be separated enters the device through inlet conduit 1, which communicates with a fermentor tank (not shown) if the products to be separated are in a fermentation broth. It may also communicate with a vessel (not shown) that holds a cell lysate or a supernatant after cell harvest. The flow rate in conduit 1 is regulated via retentate pumping means 3. The pump is any suitable pump known to those skilled in the art, and the flow rate can be adjusted in accordance with the nature of the filtration as is known to those skilled in the art.

A pressure gauge 5 is optionally employed to measure the inlet pressure of the flow from the pumping means 3. The fluid in inlet conduit 1 enters filtration unit 7. This filtration unit 7 contains a filtering chamber 7a at the top portion thereof and a filtrate chamber 7b at the bottom portion. These two compartments are divided by a filtration membrane 9. The inlet fluid flows in a direction parallel to filtration membrane 9 within filtering chamber 7a. The upper, filtering chamber 7a receives the mixture containing the species of interest. Smaller-sized species pass through the membrane 9 into the lower chamber 7b. The concentrated retentate passes from the filtration unit 7 via outlet conduit 11, where it may be collected and processed further, if necessary, to obtain the desired species of interest. Alternatively, the retentate stream is circulated back to a tank or fermentor from whence the mixture originated, to be recycled through inlet conduit 1 for further purification.

The solution containing molecules that pass through the membrane 9 into the filtrate chamber 7b leaves the filtration unit 7 via outlet conduit 13 at the same end of the filtration unit as the retentate fluid exits via outlet conduit 11. A portion of this filtrate leaves the system via conduit 13 to be discarded or sent to a second tank or vessel for further processing in a cascade mode of filtration through a membrane of smaller pore size. Optionally, a filtrate pumping means 15 is disposed within conduit 13 for this purpose. Another portion is recycled via conduit 17 to a filtrate pumping means 19, which generates the filtrate pressure gradient. This portion of the liquid is recycled via inlet conduit 21 to the inlet end of the filtrate chamber 7b such that a filtrate flow occurs in filtrate chamber 7b parallel to, and in the same direction as, the mixture being separated in filtering chamber 7a.

The operating rate of the pumping means 19 is adjusted so that the pressure at which the filtrate is introduced into chamber 7b (filtrate inlet pressure) and the pressure at which the filtrate is removed via outlet conduit 13 (filtrate outlet pressure) can be controlled to provide substantially constant TMP along the length of the membrane. The preferred procedure is to adjust the difference in pressure across chamber 7b to equal the pressure drop across chamber 7a of unit 7 to make the TMP about equal across the entire membrane. Pressure sensing means 23a and 23b can be employed at the inlet and outlet, respectively, of the recycle flow loop of filtrate through filtrate chamber 7b to monitor the pressure drop and adjust it as necessary. Pressure sensing means 23c is optionally employed in outlet conduit 11 to monitor the pressure drop for the filtering chamber 7a. The filtrate chamber 7b may include a restrictive flow path to yield an adequate pressure gradient while minimizing the filtrate circulation rate. The result of this configuration is a substantially constant TMP across the entire surface of the membrane.

The filtration unit useful herein is suitably any unit now known or discovered in the future that serves as an appropriate filtration module, particularly for microfiltration and ultrafiltration. The preferred filtration unit is hollow fibers or a flat sheet device. These sandwiched filtration units can be stacked to form a composite cell. One preferred type of rectangular filtration plate type cell is available from Filtron Technology Corporation, Northborough, Mass., under the trade name Centrasette.

Another suitable filtration unit is the Millipore Pellicon ultrafiltration system available from Millipore, Bedford, Mass.

Figure 2A:
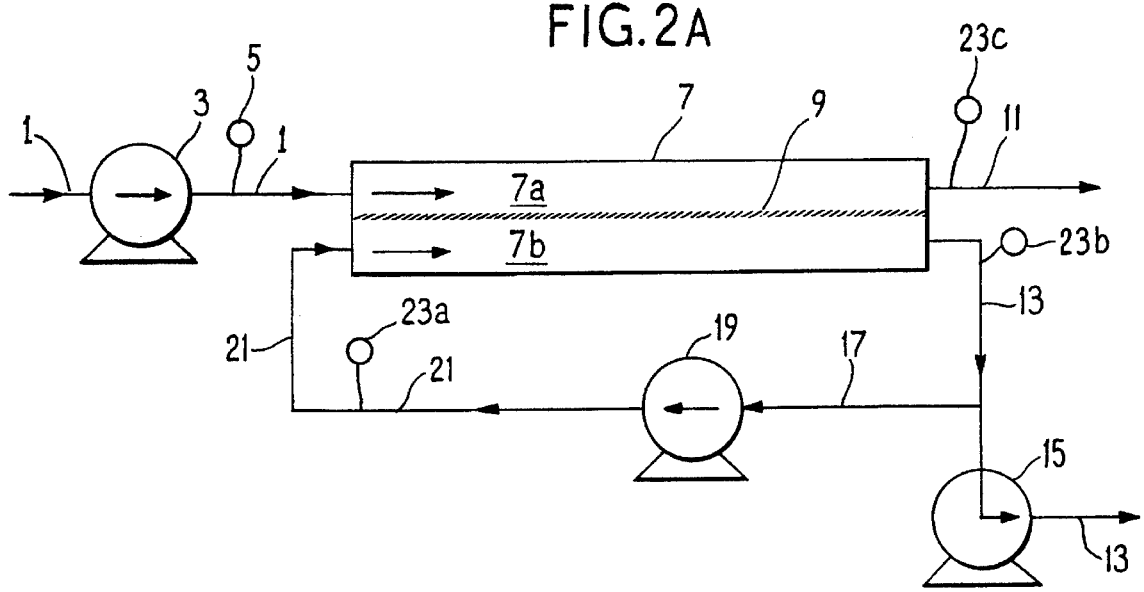
FIG. 2A depicts a schematic diagram of one apparatus useful for carrying out the high-performance tangential-flow filtration process of this invention wherein two pumps are employed on the filtrate chamber of the filtration unit and one pump is used in the retentate compartment of the filtration unit.

In the configuration shown in FIG. 2A, the membranes will need to be placed with respect to chambers 7a and 7b to provide the indicated flow rates and pressure differences across the membrane. The membranes useful in the process of this invention are generally in the form of flat sheets, rolled-up sheets, cylinders, concentric cylinders, ducts of various cross-section and other configurations, assembled singly or in groups, and connected in series or in parallel within the filtration unit. The apparatus generally is constructed so that the filtering and filtrate chambers run the length of the membrane.

Suitable membranes are those that separate the desired species from undesirable species in the mixture without substantial clogging problems and at a rate sufficient for continuous operation of the system. Examples are described by Gabler, supra. They are typically synthetic membranes of either the microporous type or the ultrafiltration type. A microporous membrane has pore sizes typically from 0.1 to 10 micrometers, and can be made so that it retains all particles larger than the rated size. Ultrafiltration membranes have smaller pores and are characterized by the size of the protein that will be retained. They are available in increments from 1000 to 1,000,000 Dalton nominal molecular weight limits.

Ultrafiltration membranes are most commonly suitable for use in the process of this invention. Ultrafiltration membranes are normally asymmetrical with a thin film or skin on the upstream surface that is responsible for their separating power. They are commonly made of regenerated cellulose or polysulfone.

Membrane filters for tangential-flow filtration are available as units of different configurations depending on the volumes of liquid to be handled, and in a variety of pore sizes. Particularly suitable for use in the present invention, on a relatively large scale, are those known, commercially available tangential-flow filtration units.

Figure 2B:
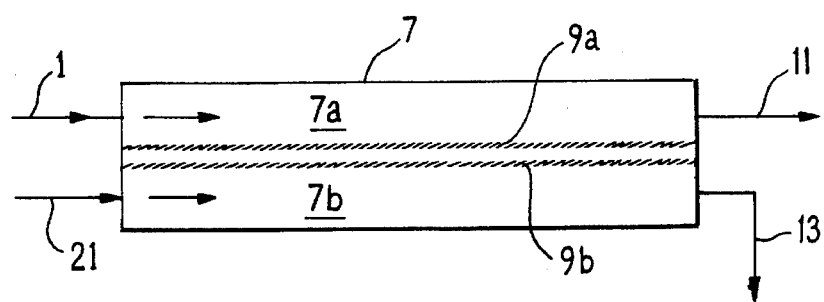
FIG. 2B depicts the filtration unit of FIG. 2A wherein two layered, parallel membranes are used in place of one.

In an alternative and preferred apparatus, and for the reasons presented above, the filtration unit 7 of FIG. 2A comprises multiple, preferably two, filtration membranes, shown in FIG. 2B as membranes 9a and 9b, respectively. These membranes are layered in a parallel configuration.

The invention also contemplates a multi-stage cascade process wherein the filtrate from the above process is passed through a filtration membrane having a smaller pore size than the membrane of the first apparatus in a second tangential-flow filtration apparatus, the filtrate from this second filtration is recycled back to the first apparatus, and the process is repeated.

In this cascade process, the second filtration typically is a conventional filtration, wherein the flux is held at a level greater than about 100% of transition point flux; also, generally the TMP is not held substantially constant along the membrane.

In a more preferred embodiment of the cascade process, both stages involve tangential-flow ultrafiltration, wherein the pore size is from 1 to 1000 kDa.

In a three-stage cascade process the filtrate from the second filtration is passed through a filtration membrane having a pore size that is less than that of the second membrane in a third tangential-flow filtration apparatus, the filtrate from this third filtration is recycled back to the first filtration apparatus, and the process is repeated. If only two high-performance filtrations are needed in the cascade process, then the third stage is conventional, i.e., the flux is held at a level greater than about 100% of transition point flux in this third stage.

In a more preferred embodiment of this three-stage cascade process, all three stages involve tangential-flow ultrafiltration.

Figure 3:
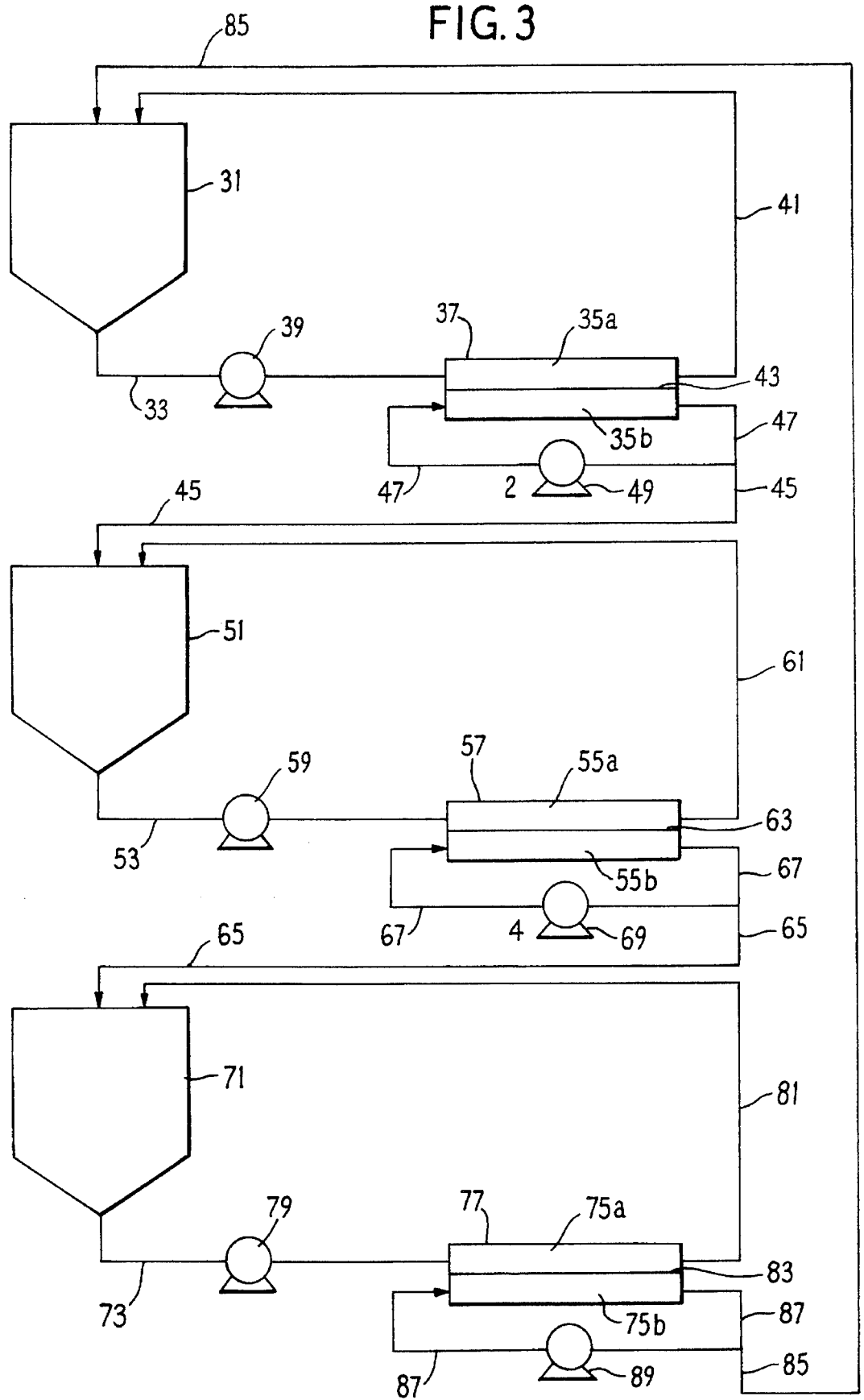
FIG. 3 depicts a schematic diagram of an apparatus that can be used for a three-stage cascade tangential-flow filtration process.

One tangential-flow apparatus suitable for conducting the cascade process is shown in FIG. 3. Here, a first vessel 31 is connected via inlet conduit 33 to a filtering chamber 35a disposed within a filtration unit 37. A first input pumping means 39 is disposed between the first vessel 31 and filtering chamber 35a. The filtering chamber 35a is connected via an outlet conduit 41 to the first vessel 31. The filtering chamber 35a is separated from a first filtrate chamber 35b situated directly below it within filtration unit 37 by a first filtration membrane 43. The first filtrate chamber 35b has an outlet conduit 47 connected to the inlet of chamber 35b with a filtrate pumping means 49 disposed in the conduit 47. Conduit 45, which is connected to outlet conduit 47, is connected also to second vessel 51.

This vessel 51 is connected via inlet conduit 53 to a second filtering chamber 55a disposed within a second filtration unit 57. A second input pumping means 59 is disposed between the second vessel 51 and filtering chamber 55a. The filtering chamber 55a is separated from the second filtrate chamber 55b situated directly below it within filtration unit 57 by a second filtration membrane 63. The second filtrate chamber 55b has an outlet conduit 67 connected to the inlet of chamber 55b with a filtrate pumping means 69 disposed in the conduit 67. Conduit 65, which is connected to outlet conduit 67, is connected also to third vessel 71.

This vessel 71 is connected via inlet conduit 73 to a third filtering chamber 75a disposed within a third filtration unit 57. A third input pumping means 79 is disposed between the third vessel 71 and filtering chamber 75a. The filtering chamber 75a is separated from the third filtrate chamber 75b situated directly below it within filtration unit 77 by a third filtration membrane 83. The third filtrate chamber 75b has an outlet conduit 87 connected to conduit 85, which is connected to first vessel 31, to allow the filtrate to recirculate to the original tank.

Optionally, the outlet conduit 87 of the third filtrate chamber 75b is connected to the inlet of chamber 75b with a filtrate pumping means 89 disposed in the conduit 87. T h e flow of fluid from the inlets to the outlets of all chambers is parallel and in the same direction. Moreover, the first filtration membrane 43 has a pore size that retains species of a larger size than that of the second and third filtration membranes 63 and 83, respectively, and the second filtration membrane 63 has a pore size that retains species of a larger size than the third filtration membrane 83.

Figure 4A:
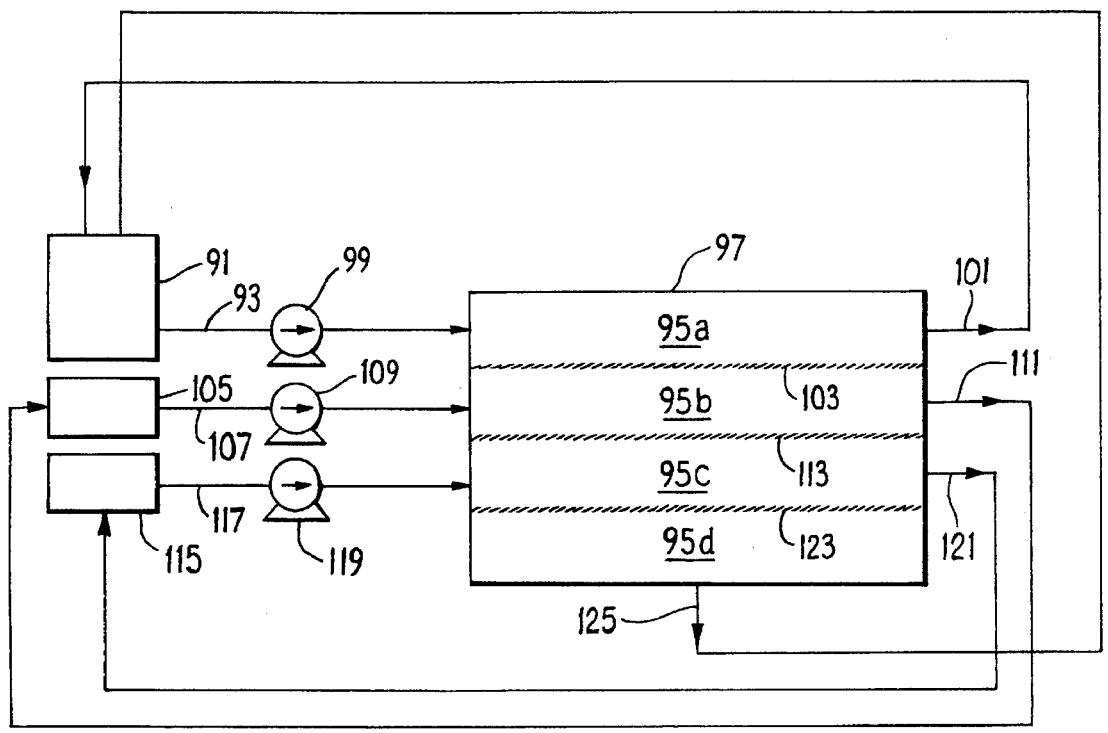
FIG. 4A depicts a schematic diagram of an alternative apparatus requiring only three pumps that can be used for a three-stage cascade tangential-flow filtration process.

A second tangential-flow apparatus suitable for conducting the cascade process is shown in FIG. 4A. Here, a first vessel 91 is connected via inlet conduit 93 to a filtering chamber 95a disposed within a filtration unit 97. A first input pumping means 99 is disposed between the first vessel 91 and filtering chamber 95a. The filtering chamber 95a is connected via an outlet conduit 101 to the first vessel 91. The filtering chamber 95a is separated from a first filtering/filtrate chamber 95b situated directly below it within filtration unit 97 by a first filtration membrane 103.

A second vessel 105 is connected via inlet conduit 107 to the first filtering/filtrate chamber 95b. A second input pumping means 109 is disposed between the second vessel 105 and first filtering/filtrate chamber 95b. The first filtering/filtrate chamber 95b is connected via an outlet conduit 111 to the second vessel 105. The first filtering/filtrate chamber 95b is separated from a second filtering/filtrate chamber 95c situated directly below it within filtration unit 97 by a second filtration membrane 113.

A third vessel 115 is connected via inlet conduit 117 to the second filtering/filtrate chamber 95c. A third input pumping means 119 is disposed between the third vessel 115 and the second filtering/filtrate chamber 95c. The second filtering/filtrate chamber 95c is connected via an outlet conduit 121 to the third vessel 115. The second filtering/filtrate chamber 95c is separated from a filtrate chamber 95d situated directly below it within filtration unit 97 by a third filtration membrane 123.

The filtrate chamber 95d is connected via outlet conduit 125 to the first vessel 91, to allow the filtrate to recirculate to the original vessel. The flow of fluid from the inlets to the outlets of all chambers is parallel and in the same direction. Moreover, the first filtration membrane 103 has a pore size that retains species of a larger size than that of the second and third filtration membranes 113 and 123, respectively, and the second filtration membrane 113 has a pore size that retains species of a larger size than the third filtration membrane 123.

The cascade apparatus of FIG. 4A allows for high-performance tangential-flow multiple filtrations having all the advantages therein and requiring only three pumps and one device rather than the five or six pumps and three devices that would otherwise be required for the high-performance tangential-flow filtration cascade system shown in FIG. 3.

Figure 4B:
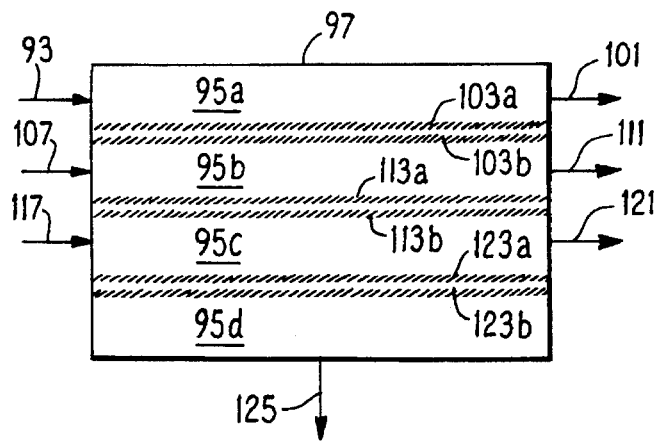
FIG. 4B depicts the filtration unit of FIG. 4A wherein two layered, parallel membranes are employed for each membrane shown in FIG. 4A.

Optionally, the apparatus of FIG. 4A is configured so that each filtration membrane constitutes a plurality of membranes, preferably two, layered parallel and on top of the other, within filtration unit 97, as shown in FIG. 4B (membrane 103b for first membrane 103a, membrane 113b for second membrane 113a, and membrane 123b for third membrane 123a ).

The cascade apparati shown in FIGS. 3 and 4 are such that the first membrane 43 or 103 has a pore size with a cut-off greater than that of the second membrane 63 or 113, respectively, which in turn has a pore size with a cut-off greater than that of the third membrane 83 or 123, respectively. Most preferably, these membranes are all ultrafiltration membranes.

The apparati of FIGS. 3 and 4A are designed to conduct a three-stage separation employing three filtration membranes. The invention herein also contemplates devices wherein only two filtration membranes and two vessels are involved, so that, for example, in FIG. 4A the second filtrating/filtrate chamber 95c is a filtrate chamber with an outlet conduit, and elements 95d, 121, 123, 115, 117, and 119 are not present. In other variations, the apparati of FIGS. 3 and 4A contain more than three filtration membranes and more than three vessels, so that, for example, the second filtrating/filtrate chamber 95c of FIG. 4A is connected via a fourth filtration membrane to a third filtrating/filtrate chamber equipped with an inlet and outlet conduit in fluid communication with a fourth vessel, and so on, with the last or bottommost chamber being a filtrate chamber like that of 95d in fluid communication via conduit 125 with the first vessel 91, as illustrated in FIG. 4A.

The process of the present invention is well adapted for use on a commercial and semi-commercial scale. It can be run in batch or continuous operations, or in a semi-continuous manner, e.g., on a continuous-flow basis of solution containing the desired species, past a tangential-flow filter, until an entire large batch has thus been filtered, with washing steps interposed between the filtration stages. Then fresh batches of solution can be treated. In this way, a continuous cycle process can be conducted to give large yields of desired product, in acceptably pure form, over relatively short periods of time.

The unique feature of tangential-flow filtration as described herein with its ability to provide continuous filtration of solids-containing solutions without filter clogging results in a highly advantageous process for separating and purifying biological reaction products for use on a continuous basis and a commercial scale. Moreover, the process is applicable to a wide range of biological molecules, e.g., proteinaceous products of fermentation with natural or genetically engineered microorganisms, high molecular weight antibodies, cellular secretions, etc.

The following examples illustrate the invention in further detail, but are not intended to be limiting. In these examples, the disclosures of all references cited are expressly incorporated by reference.

EXAMPLE I

In this example, the purification of recombinant t-PA (about 65 kDa) from Cytochrome-C (about 12.5 kDa) in conventional and high-performance tangential-flow ultrafiltration mode was compared.

A sample of recombinant t-PA (U.S. Pat. Nos. 4,766,075; 4,853,330; 4,777,043; and 4,908,205) in 0.2 M arginine phosphate buffer containing 0.002% Tween 80, pH 7.2 ( "buffer") was diluted with water to obtain two one-liter aliquots of a 0.9 mg/ml solution of rt-PA. Cytochrome-C (Sigma) was added to a final calculated concentration of 0.1 mg/ml.

For Test No. 2 below, a high-performance TFF (HP-TFF) research module essentially identical to that illustrated in FIG. 2A was employed using a membrane consisting of about 0.42 ft$^2$ of 30-kDa Hoechst Kalle regenerated cellulose to separate the rt-PA from the Cytochrome-C in the mixture. The outlet conduit 11 circulates the fluid back to a bulk vessel (30 kDa) containing the mixture connected to inlet conduit 1, and outlet conduit 13 is connected to a tank (5 kDa) in a closed loop cascade mode with a conventional Millipore Pellicon ultrafiltration system containing 10 ft$^2$ of 5 kDa regenerated cellulose membrane. This membrane retains the Cytochrome-C and provides adequate filtration rate to equal the HP-TFF module. The filtrate from the 5 kDa system was split, with one part connected to the 5 kDa retentate in a 5 kDa vessel of the Millipore system and the other part connected via a 7016 Masterflex pump to the 30 kDa bulk vessel. This pump was used to maintain constant liquid levels in both the 30 kDa and 5 kDa vessels. The research and Pellicon modules were flushed extensively with water, drained, and then primed with buffer. The 30 kDa system was then drained, integrity tested, and filled with 750 ml of the above-described mixture of rt-PA and Cytochrome-C, while the 5 kDa system was drained, integrity tested, and filled with 750 ml of buffer.

For Test No. 1 illustrating the conventional mode for comparison purposes, the 30 kDa research module/5 kDa Pellicon cascade was employed with the research module operated in a conventional ultrafiltration mode rather than the HP-TFF mode described above.

The parameters of the research module employed for both tests are given below:

| | |
|---|---|
| channel width | 3 cm |
| channel height | 0.8 mm |
| channel length | 152 cm |
| 30 kDa recirculation pump | Masterflex 7015 [6–600 rpm] (Cole Parmer, Chicago IL) peristaltic pump |
| 30 kDa filtration pump | None |
| 30 kDa recirculating filtrate pump | Double-headed Masterflex 7015 [6–600 rpm] |

-continued

| | |
|---|---|
| 5 kDa recirculation pump | Masterflex 7019 (Cole Parmer, Chicago IL) peristaltic pump |
| 5 kDa filtration pump | Masterflex 7016 [6–600 rpm] (Cole Parmer, Chicago IL) peristaltic pump |
| 30 kDa regenerated cellulose membrane | Hoechst Kalle roll stock lot #228 |
| 5 kDa regenerated cellulose membrane | Millipore lot #C9CK7889 |

Tests 1 and 2 were performed under the different conditions listed below, where $Q_s$ is feed rate, $Q_{H2O}$ is water filtration rate, $Q_f$ is process filtration rate, and $Q_{rf}$ is recirculating filtrate rate.

Test No. 1

30-kDa integrity test: $\Delta P = 0.1$ psi in 1 min. at $P_o = 5$ psi; $Q_{H2O}/TMP = 10.71$ ml/min, psi; retentate temperature = 23° C.
5-kDa integrity test: $\Delta P = 0.1$ psi in 1 min. at $P_o = 5$ psi; $Q_{H2O}/TMP = 7.50$ ml/min., psi; retentate temperature = 22° C.
  Qs − Qf = 305 ml/min
  Qrf = 0 ml/min.
  Qf = 93 ml/min.
  Qs = 398 ml/min.

| | Module Length [−] | 0.00 | 0.25 | 0.50 | 0.75 | 1.00 |
|---|---|---|---|---|---|---|
| Start | Retentate Pressure | 31.6 | 28.0 | 24.2 | 21.8 | 20.0 |
| | Filtrate Pressure | 1.0 | 0.9 | 0.8 | 0.5 | 0.3 |
| | ΔTMP | 30.6 | 27.1 | 23.4 | 21.3 | 19.7 |
| End | Retentate Pressure | 29.9 | 26.6 | 23.3 | 21.1 | 19.7 |
| | Filtrate Pressure | 0.9 | 0.8 | 0.7 | 0.4 | 0.2 |
| | ΔTMP | 29.0 | 25.8 | 22.6 | 20.7 | 19.5 |

Pellicon 5 kDa; $P_i = 34$ psi; $P_o = 20.0$ psi.
30-kDa integrity test: $\Delta P = 0.1$ psi in 1 min. at $P_o = 5$ psi; retentate temperature = 28° C.
5-kDa integrity test: $\Delta P = 0.2$ psi in 1 min. at $P_o = 5$ psi; retentate temperature = 35° C.

Test No. 2

30-kDa integrity test: $\Delta P = 0.1$ psi in 1 min. at $P_o = 5$ psi, where $P_o$ is outlet pressure; $Q_{H2O}/TMP = 10.86$ ml/min, psi; retentate temperature = 23° C.
5-kDa integrity test: $\Delta P = 0.1$ psi in 1 min. at $P_o = 5$ psi; $Q_{H2O}/TMP = 8.89$ ml/min, psi; Retentate temperature = 23°C.
  Qs − Qf = 360.5 ml/min
  Qrf = 847.0 ml/min
  Qf = 83 ml/min
  Qs = 443.5 ml/min

| | Module Length [−] | 0.00 | 0.25 | 0.50 | 0.75 | 1.00 |
|---|---|---|---|---|---|---|
| Normalized | | | | | | |
| Start | Retentate Pressure | 30.7 | 25.7 | 20.4 | 16.9 | 14.6 |
| | Filtrate Pressure | 17.1 | 13.4 | 10.4 | 6.1 | 1.7 |
| | ΔTMP | 13.6 | 12.3 | 10.0 | 10.8 | 12.9 |
| End | Retentate Pressure | N.D.* | N.D. | N.D. | N.D. | N.D. |
| | Filtrate Pressure | N.D. | N.D. | N.D. | N.D. | N.D. |
| | ΔTMP | 13.6 | N.D. | N.D. | N.D. | 13.5 |

*N.D. = not determined.
Pellicon 5 kDa; $P_i$ (inlet pressure) = 35 psi;
$P_o$ (outlet pressure) = 19.0 psi.
30-kDa integrity test: $\Delta P = 0.1$ psi in 1 min. at $P_o = 5$ psi;

-continued

Test No. 2 retentate temperature = 33° C.
5-kDa integrity test: ΔP = 0.1 psi in 1 min. at Po = 5 psi; retentate temperature = 40° C.

Two different assays were performed for tests 1 and 2. In the first assay, the $A_{280\ nm}$ and $A_{410\ nm}$ were determined for the starting and ending bulks. The Cytochrome-C concentration was determined by $A_{410\ nm}$ (t-PA does not absorb at 410 nm). The t-PA concentration was then determined at $A_{280\ nm}$ after subtracting the $A_{280\ nm}$ absorbance due to Cytochrome-C.

In the second assay, the starting bulk (mixture before recirculation) and ending bulk and retentates for the 30-kDa tank at 1, 5, and 9 diavolumes were assayed by TSK-200 size-exclusion HPLC with detection at 214 nm.

The results are as follows:

$A_{410nm}$=0.41551×2={epsilon$_{Cytochrome-C,410\ nm}$=8.9}= 0.0934 mg/ml Cytochrome-C.

$A_{280nm}/A_{410nm}$ Assay:

Test 1: Conventional Mode

| | | | |
|---|---|---|---|
| 30 kDa Start Bulk | t-PA | 722.5 mg | 100% |
| | Cytochrome-C | 86.0 mg | 100% |
| 5 kDa Start Bulk | t-PA | 0.0 mg | 0% |
| | Cytochrome-C | 0.0 mg | 0% |
| 30 kDa End Bulk | t-PA | 642.6 mg | 89% yield |
| | Cytochrome-C | 11.5 mg | 7.5-fold purif. |
| 5 kDa End Bulk | t-PA | 58.0 mg | 8% loss |
| | Cytochrome-C | 60.3 mg | 70% yield |
| Mass Balance | t-PA | 700.6 mg | 97% |
| | Cytochrome-C | 71.8 mg | 83% |

Test 2: High-Performance Mode

| | | | |
|---|---|---|---|
| 30 kDa Start Bulk | t-PA | 753.3 mg | 100% |
| | Cytochrome-C | 82.2 mg | 100% |
| 5 kDa Start Bulk | t-PA | 0.0 mg | 0% |
| | Cytochrome-C | 0.0 mg | 0% |
| 30 kDa End Bulk | t-PA | 653.9 mg | 87% yield |
| | Cytochrome-C | 2.1 mg | 38-fold purif. |
| 5 kDa End Bulk | t-PA | 107.8 mg | 14% loss |
| | Cytochrome-C | 73.8 mg | 90% yield |
| Mass Balance | t-PA | 761.7 mg | 101% |
| | Cytochrome-C | 75.9 mg | 92% |

These results show that the HP-TFF gave a substantially increased fold purification over C-TFF.

Figure 5:
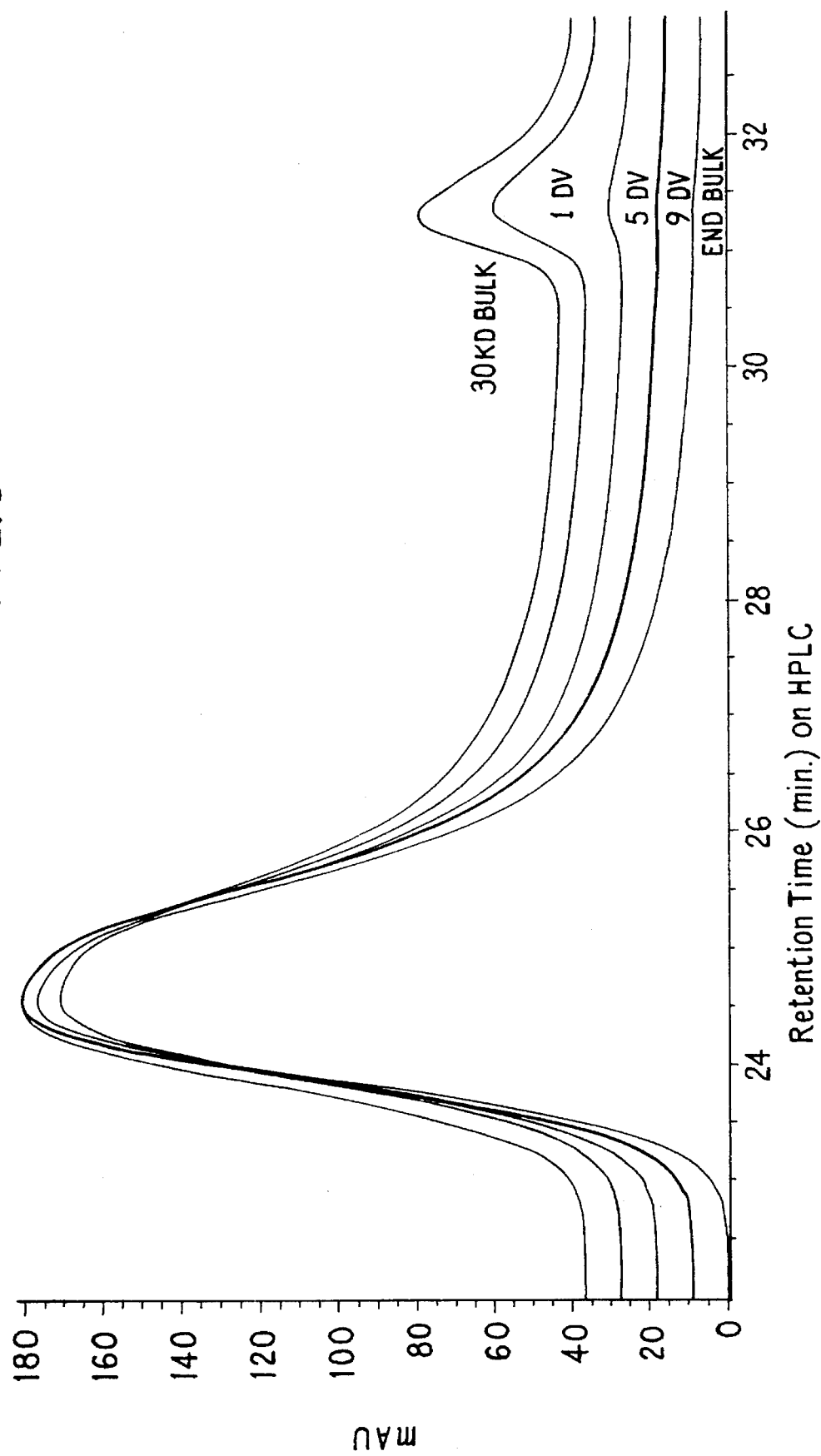
FIG. 5 depicts an HPLC chromatogram of retentate samples from a run similar to that used for FIG. 6 for the start bulk solution (30 kD bulk), 1, 5, and 9 diavolumes (DV) of filtration, and the end bulk solution, with the first peak indicating t-PA and the second peak indicating Cytochrome-C.

A series of HPLC chromatograms illustrating the removal of Cytochrome-C from rt-PA is shown in FIG. 5. The graph shows the clean separation of t-PA from Cytochrome-C, a molecule less than ten-fold less in molecular weight than t-PA.

EXAMPLE II

This example shows a study designed to determine sieving of rt-PA and Cytochrome-C in a mixture as a function of TMP in both conventional and high-performance tangential-flow ultrafiltration using a 30 kDa molecular weight cut-off membrane. The flux was determined for each operating condition. Based on sieving values, the theoretical purification and yield that can be obtained by either tangential-flow ultrafiltration method was determined as a function of diavolumes using the 30-kDa/5-kDa cascade tangential-flow ultrafiltration system described in Example I.

In addition, this example examines the effect of increased recirculation rate on purification.

The retentate and filtrate from Example I were recombined and concentrated on a 5-kDa Pellicon system. The retentate from this concentration was 0.2 μm filtered and stored in the cold room (2°–8° C.)

The research module described in Example I (about 0.42 ft$^2$ of 30-kDa Hoechst Kalle regenerated cellulose) was operated in a total recycle mode. The research module was flushed extensively with water, drained, and then primed with buffer. The 30-k Da system was then drained, integrity tested, and filled with about 750 ml of the mixture of rt-PA and Cytochrome-C of Example I.

For each test, filtration was run for ten minutes with flux measurements performed at 5 and 10 minutes to ensure stable flux conditions. Samples of retentate and filtrate were taken at 10 minutes and subjected to HPLC analysis.

All experiments were run at an outlet pressure ($P_o$) of about 20 psi and inlet pressures ($P_i$) of either 35 or 50 psi (ΔP about 15 and 30 psi). For HP-TFF with recirculating filtrate pump, the TMP was set for 5 and 10 psi at ΔP of both 15 and 30 psi. Tests were also done using HP-TFF without recirculating filtrate pump at $P_o$=1 psi and ΔP about 15 and 30 psi. The 30 kDa recirculation pump, filtration pump, recirculating filtrate pump, regenerated cellulose membrane, and fluid were the same as described in Example I. 30-kDa integrity test: ΔP=0.1 psi in 1 min. at $P_o$=5 psi; $Q_{H2O}$/TMP=not determined; retentate temperature=22° C.

Test 1:

Test 1 uses the research module operated in a high-performance mode at $P_o$=20 psi, ΔP about 30 psi, and TMP about 5 psi. A low TMP condition was obtained by recirculating filtrate with back pressure on the filtrate outlet.

| | | | | | |
|---|---|---|---|---|---|
| | Qs − Qf = 531 ml/min | | | | |
| | Qrf = 1093 ml/min | | | | |
| | Qf = 67 ml/min | | | | |
| | Qs = 598 ml/min | | | | |
| Module Length [−] | 0.00 | 0.25 | 0.50 | 0.75 | 1.00 |
| Retentate Pressure | 47.0 | 39.0 | 30.6 | 24.6 | 20.1 |
| Filtrate Pressure | 36.4 | 31.3 | 27.0 | 21.2 | 14.9 |
| ΔTMP | 10.6 | 7.7 | 3.6 | 3.4 | 5.2 |

Filtration rate = 67 ml/min ⟹ Flux = 9.57 l/square foot and hour; retentate temperature = 31° C.

Test 2:

Test 2 uses the research module operated in a high-performance mode at $P_o$ about 20 psi, ΔP about 30 psi, and a TMP of about 10 psi.

| | | | | | |
|---|---|---|---|---|---|
| | Qs − Qf = 480 ml/min. | | | | |
| | Qrf = 1086 ml/min | | | | |
| | Qf = 87 ml/min | | | | |
| | Qs = 567 ml/min | | | | |
| Module Length [−] | 0.00 | 0.25 | 0.50 | 0.75 | 1.00 |
| Retentate Pressure | 44.6 | 37.1 | 29.4 | 24.0 | 20.1 |
| Filtrate Pressure | 32.4 | 27.3 | 23.0 | 17.0 | 10.0 |
| ΔTMP | 12.2 | 9.8 | 6.4 | 7.0 | 10.1 |

Filtration rate = 87 ml/min ⟹ Flux = 12.4 l/square foot and hour; retentate temperature = 32° C.

Test 3:

Test 3 uses the research module operated in a conventional mode at $P_o$ about 20 psi and ΔP about 30 psi.

|  | Qs − Qf = 493 ml/min | | | | |
|---|---|---|---|---|---|
|  | Qrf = 0 ml/min. | | | | |
|  | Qf = 118 ml/min. | | | | |
|  | Qs = 611 ml/min. | | | | |
| Module Length [−] | 0.00 | 0.25 | 0.50 | 0.75 | 1.00 |
| Retentate Pressure | 42.2 | 34.6 | 27.1 | 21.8 | 17.8 |
| Filtrate Pressure | 1.2 | 1.2 | 1.1 | 0.8 | 0.4 |
| ΔTMP | 41.0 | 33.4 | 26.0 | 21.0 | 17.4 |

Filtration rate = 118 ml/min ==> Flux = 16.9 l/square foot and hour; retentate temperature = 29° C.

Test 4:

Test 4 uses the research module operated in a high-performance mode at $P_o$ about 20 psi, ΔP about 15 psi, and a TMP of about 5 psi.

|  | Qs − Qf = 377 ml/min | | | | |
|---|---|---|---|---|---|
|  | Qrf = 878 ml/min | | | | |
|  | Qf = 46 ml/min | | | | |
|  | Qs = 423 ml/min | | | | |
| Module Length [−] | 0.00 | 0.25 | 0.50 | 0.75 | 1.00 |
| Retentate Pressure | 35.6 | 30.9 | 26.0 | 22.6 | 20.0 |
| Filtrate Pressure | 29.6 | 26.3 | 23.3 | 19.2 | 15.4 |
| ΔTMP | 6.0 | 4.6 | 2.7 | 3.4 | 4.6 |

Filtration Rate = 46 ml/min ==> Flux = 6.57 l/square foot and hour; retentate temperature = 30° C.

Test 5:

Test 5 uses the research module operated in a high-performance mode at $P_o$ =20 psi, ΔP=15 psi, and a TMP of about 10 psi.

|  | Qs − Qf = 361 ml/min | | | | |
|---|---|---|---|---|---|
|  | Qrf = 886 ml/min | | | | |
|  | Qf = 74 ml/min. | | | | |
|  | Qs = 435 ml/min. | | | | |
| Module Length [−] | 0.00 | 0.25 | 0.50 | 0.75 | 1.00 |
| Retentate Pressure | 35.2 | 30.3 | 25.3 | 21.9 | 19.5 |
| Filtrate Pressure | 24.0 | 20.5 | 17.3 | 12.8 | 8.3 |
| ΔTMP | 11.2 | 9.8 | 8.0 | 9.1 | 11.2 |

Filtration rate = 74 ml/min ==> Flux = 10.6 l/square foot and hour; retentate temperature = 30° C.

Test 6:

Test 6 operates in a conventional mode at $P_o$=20 psi and ΔP=15 psi.

|  | Qs − Qf = 361 ml/min | | | | |
|---|---|---|---|---|---|
|  | Qrf = 0 ml/min. | | | | |
|  | Qf = 80 ml/min. | | | | |
|  | Qs = 441 ml/min. | | | | |
| Module Length [−] | 0.00 | 0.25 | 0.50 | 0.75 | 1.00 |
| Retentate Pressure | 35.0 | 30.4 | 25.8 | 22.6 | 20.1 |
| Filtrate Pressure | 0.7 | 0.7 | 0.6 | 0.5 | 0.2 |
| ΔTMP | 34.3 | 29.7 | 25.2 | 22.1 | 19.9 |

Filtration Rate = 80 ml/min ==> Flux = 11.4 l/square foot and hour; retentate temperature = 27° C.

Test 7:

Test 7 was conducted at $P_o$=1 psi and ΔP=15 psi.

|  | Qs − Qf = 343 ml/min | | | | |
|---|---|---|---|---|---|
|  | Qrf = 0 ml/min | | | | |
|  | Qf = 51 ml/min | | | | |
|  | Qs = 394 ml/min | | | | |
| Module Length [−] | 0.00 | 0.25 | 0.50 | 0.75 | 1.00 |
| Retentate Pressure | 16.2 | 11.8 | 7.1 | 3.9 | 1.5 |
| Filtrate Pressure | 0.5 | 0.4 | 0.4 | 0.3 | 0.1 |
| ΔTMP | 15.7 | 11.4 | 6.7 | 3.6 | 1.4 |

Filtration Rate = 51 ml/min ==> Flux = 7.29 l/square foot and hour; retentate temperature = 23° C.

Test 8:

Test 8 was operated at $P_o$=1 psi and ΔP=30 psi.

|  | Qs − Qf = 555 ml/min | | | | |
|---|---|---|---|---|---|
|  | Qrf = 0 ml/min | | | | |
|  | Qf = 77 ml/min | | | | |
|  | Qs = 632 ml/min | | | | |
| Module Length [−] | 0.00 | 0.25 | 0.50 | 0.75 | 1.00 |
| Retentate Pressure | 33.2 | 24.8 | 15.4 | 8.6 | 3.5 |
| Filtrate Pressure | 0.8 | 0.7 | 0.6 | 0.4 | 0.1 |
| ΔTMP | 32.4 | 24.1 | 14.8 | 8.2 | 3.4 |

Filtration Rate = 77 ml/min ==> Flux = 11.0 l/square foot and hour; retentate temperature = 24° C.

After each test and prior to cleaning, an integrity test was performed: ΔP=0.1 psi in 1 min. at $P_o$=5 psi. The post-cleaning filtration rate/TMP for storage solution was 30 kDa Qf/TMP=9.6 ml/min, psi.

The following samples were taken during the tests and assayed by the HPLC method described in Example I.

Sample rt-PA/Cytochrome-C mix before recirculation 30 kDa bulk, tests 1–8 30 kDa filtrate, tests 1–8

The data are summarized below:

| Test No. | Mode HP/C | Rate ml/m | ΔP psi | TMP psi | Jf LSFH | Temp. °C. | Jf, 30° C. LSFH | RtPA [–] | RcytC [–] |
|---|---|---|---|---|---|---|---|---|---|
| 1 | HP | 598 | 26.9 | 6.1 | 9.57 | 31 | 9.37 | >.996 | .807 |
| 2 | HP | 567 | 24.5 | 9.1 | 12.4 | 32 | 11.9 | >.996 | .783 |
| 3 | C | 611 | 24.4 | 27.8 | 16.9 | 29 | 17.3 | >.996 | .888 |
| 4 | HP | 423 | 15.6 | 4.3 | 6.57 | 30 | 6.57 | >.997 | .796 |
| 5 | HP | 435 | 15.7 | 9.9 | 10.6 | 30 | 10.6 | .997 | .790 |
| 6 | C | 441 | 14.9 | 26.2 | 11.4 | 27 | 12.2 | >.998 | .941 |
| 7 | HP | 394 | 14.7 | 7.8 | 7.3 | 23 | 8.52 | >.998 | .809 |
| 8 | HP | 632 | 29.7 | 16.6 | 11.0 | 24 | 12.6 | >.998 | .840 |

"Mode" is either High-Performance [HP] or Conventional [C].
"ΔP" is pressure drop from retentate inlet to outlet.
"TMP" is average transmembrane pressure.
"Jf" is measured flux.
"LSFH" is liters/square foot, hour
"Temp." is bulk temperature measured at time of flux measurement.
"Jf, 30° C." is corrected flux at 30° C. calculated based on correction factors from Prostak ™ Maintenance, page 15.
"RtPA" is rt-PA retention measured by TSK-2000 HPLC with peak integration at 214 nm.?
"RCytC" is Cytochrome-C retention measured by TSK-2000 HPLC with peak integration at 214 nm.
"Yield" is theoretical yield of rt-PA in a closed loop cascade system with a 30-kDa high-performance tangential-flow ultrafiltration first stage. It is calculated by the formula: Yield = 100% $e^{DV(RtPA - 1)}$.
"Purif." is calculated fold purification of rt-PA (removal of Cytochrome-C) in the same system, using the formula: Purification = $e^{DV(1 - RcytC)}$.

Results

Figure 6:
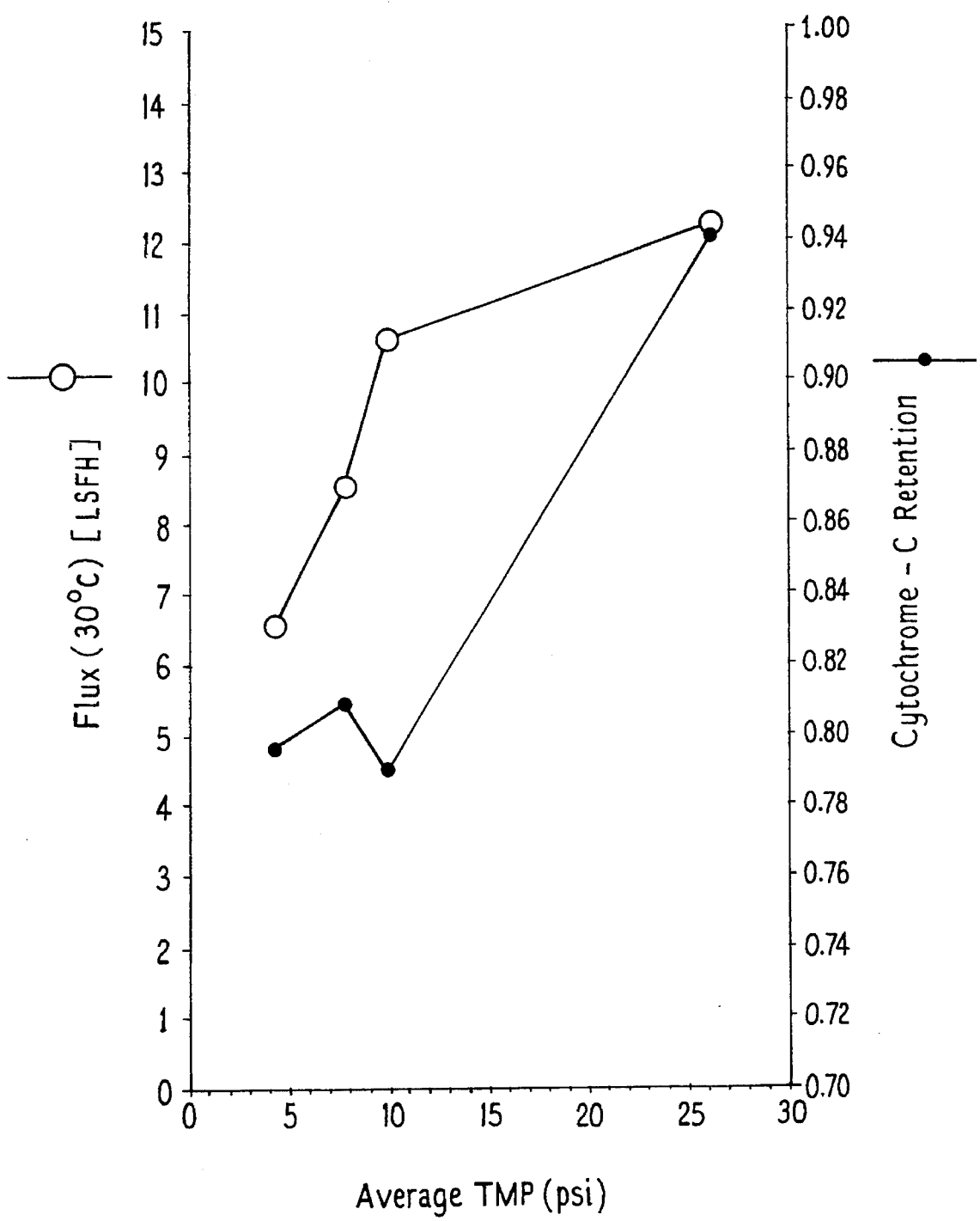
FIG. 6 illustrates a graph of flux at 30° C. (open circles) and Cytochrome-C retention (solid circles) versus average TMP for separating t-PA from Cytochrome-C.

A graph of flux at 30° C. (open circles) and Cytochrome-C retention (solid circles) versus average TMP from the data above is shown in FIG. 6. It can be seen that the Cytochrome-C retention increases with increased TMP from 10 psi to 27 psi, and the flux increases dramatically from 4 psi to 10 psi TMP and then starts to level off from 10 to 27 psi TMP.

Tests 1, 2, 4, and 5 use recirculating filtrate in the HP-TFF mode, where the TMP is substantially constant across the entire membrane surface. The results show lower retention of Cytochrome-C for these tests than that for the HP-TFF without recirculating filtrate (Tests 7–8) and for C-TFF (Tests 3 and 6).

Test Nos. 7–8 were designed to see if good purification could be obtained in the pressure-dependent part of the flux versus TMP curve without using recirculating filtrate (where the TMP decreases across the entire membrane surface), as compared to conventional C-TFF, which is operated in the pressure-independent part of the curve. The results show that this is the case (compare the retention of Cytochrome-C for tests 7–8 with that for tests 3 and 6 using the conventional mode).

Figure 7:
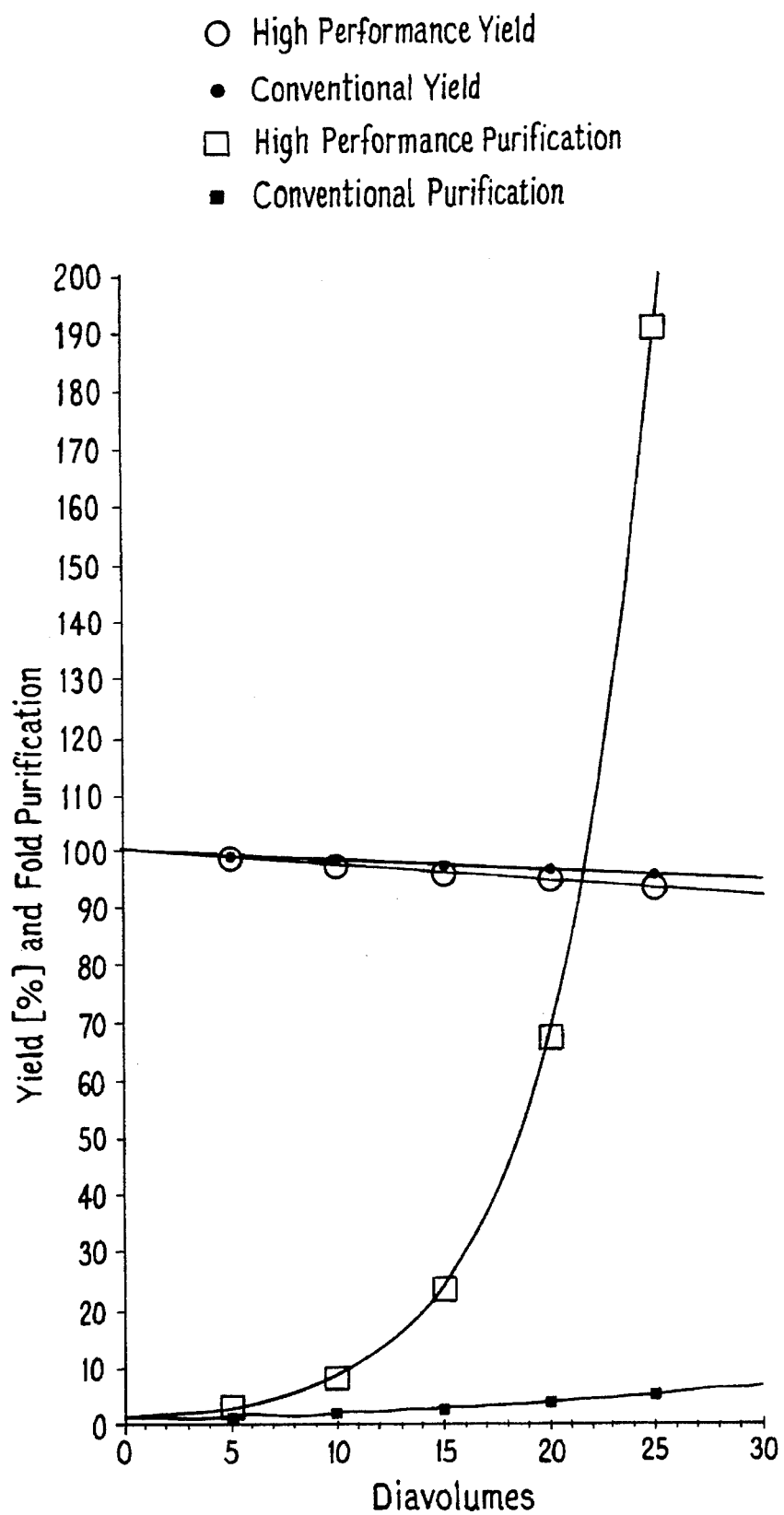
FIG. 7 depicts a graph of the calculated percent yield and fold purification versus diavolumes for conventional tangential-flow ultrafiltration (C-TFF) without a constant TMP (solid circles for yield and solid squares for purification) and for high-performance tangential-flow ultrafiltration (HP-TFF) (open circles for yield and open squares for purification).
Figure 8:
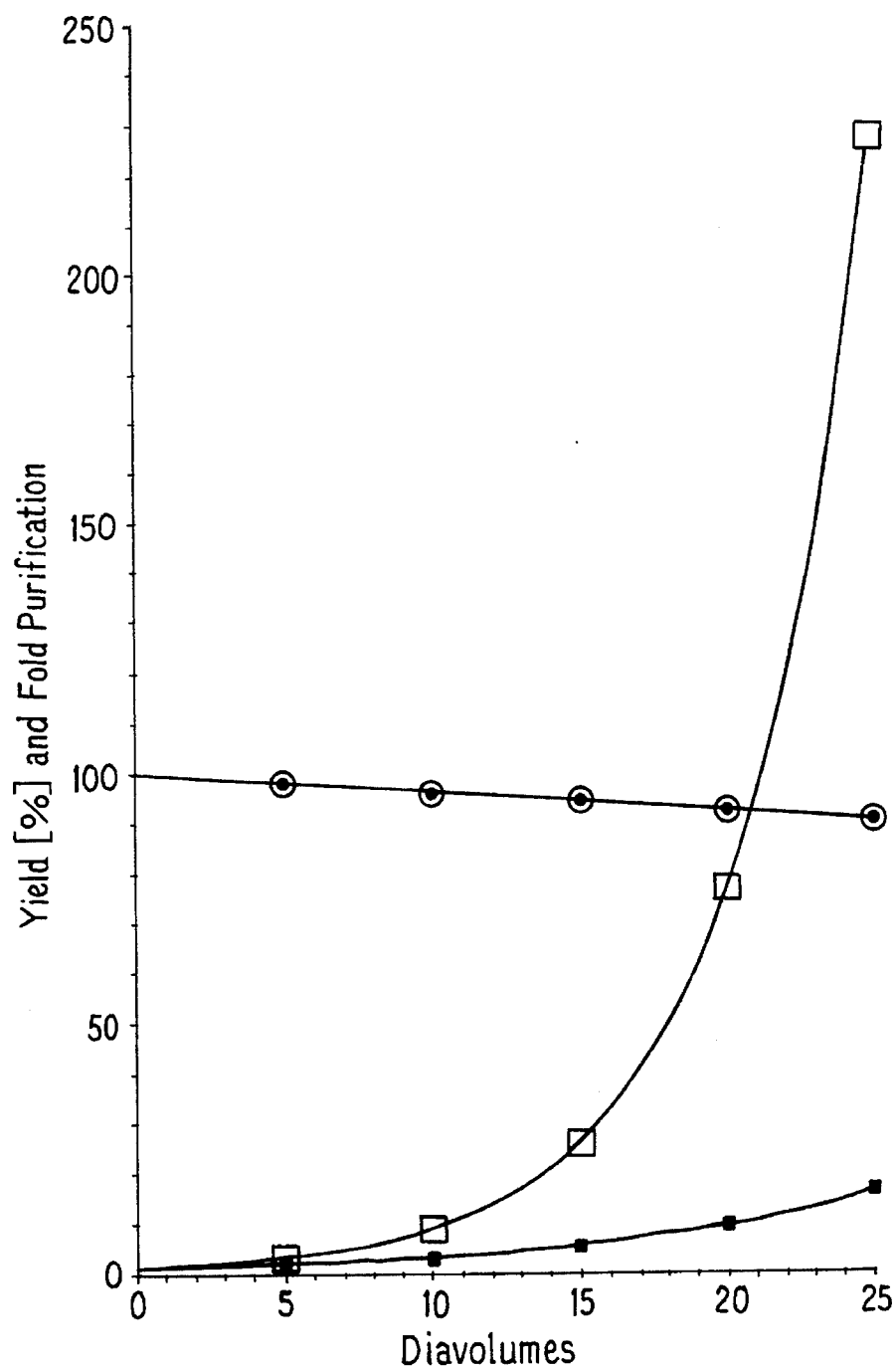
FIG. 8 depicts a graph of the calculated percent yield and fold purification versus diavolumes for C-TFF and HP-TFF using a higher recirculation rate than was used to generate FIG. 7.

Tests 1–3 and 8 utilize a recirculation rate of 600 ml/min on average, and Tests 4–7 use a recirculation rate of 425 ml/min on average. The calculated results of recycling filtrate using the recirculating pump are seen in FIGS. 7 and 8 for Test Nos. 5–6 and 2–3, respectively. The open squares indicate the theoretical high-fold purification that can be achieved using high-performance TFF, versus the low-fold purification using conventional purification (solid squares). The product yields in circles do not appear to be dramatically different with increasing diavolumes of mixture. FIG. 7 shows the difference between C-TFF and HP-TFF at the lower recirculation rate. One way that others have attempted to reduce concentration polarization attendant TFF is by increasing linear velocity (recirculation rate). Test Nos. 2–3 were designed to show if HP-TFF was still improved over conventional TFF at higher recirculation rates. FIG. 8 shows that HP-TFF results in greater-fold purification than C-TFF under the same conditions of high linear velocity.

In summary, the calculations indicated that good yields (>90%) of a retained species could be obtained with a closed loop ultrafiltration cascade system at 25 diavolumes. Retention data indicate that a 190-fold removal of Cytochrome-C (R=0.79) from rt-PA (R=0,997) could be obtained using the novel ultrafiltration tangential-flow ultrafiltration method operated in a cascade mode with 25 diavolumes, using a Hoechst Kalle 30 kDa regenerated cellulose membrane in the first stage and a Cytochrome-C retentive membrane in the second stage (operated in conventional ultrafiltration mode).

EXAMPLE III

This experiment is designed to determine retention of arginine (molecular weight 174 Dalton), Cytochrome-C (12.5 kDa), rh-GH (22 kDa), and rt-PA (65 kDa) versus TMP using a 30-k Da regenerated cellulose membrane in a short pathlength experimental module. A short pathlength was used to minimize the difference in inlet and outlet TMP. The efficiency of the separation of these molecules in a research module was compared under HP-TFF and C-TFF conditions.

The protein solution employed consisted of 1 mg/ml rt-PA (see Example I), 1 µg/ml recombinant human growth hormone without an N-terminal methionine, and 0.1 mg/ml Cytochrome-C in 0.2 M arginine phosphate buffer, pH 7.5.

The short pathlength experimental module employed had the following parameters:

| | |
|---|---|
| channel width | 3 cm |
| channel height | 0.8 mm |
| channel length | 6 cm |
| membrane | 30 kDa regenerated cellulose |
| recirculation rate | 760 ml/min. |
| pump | Masterflex (Cole Parmer, Chicago IL) peristaltic pump |

This module differs from the research module employed in Example I in that the channel length is 6 cm rather than 152 cm.

For comparison of separation using C-TFF and HP-TFF, the research module of Example I was employed. For C-TFF the outlet pressure was set to 20 psig. The resulting inlet pressure was 50 psig at a feed rate of 760 ml/min. The average TMP was 35 psi. For HP-TFF the TMP was set at 17 psi. The recirculating filtrate rate was regulated at a rate that provided the most constant TMP along the length of the membrane.

Figure 9:
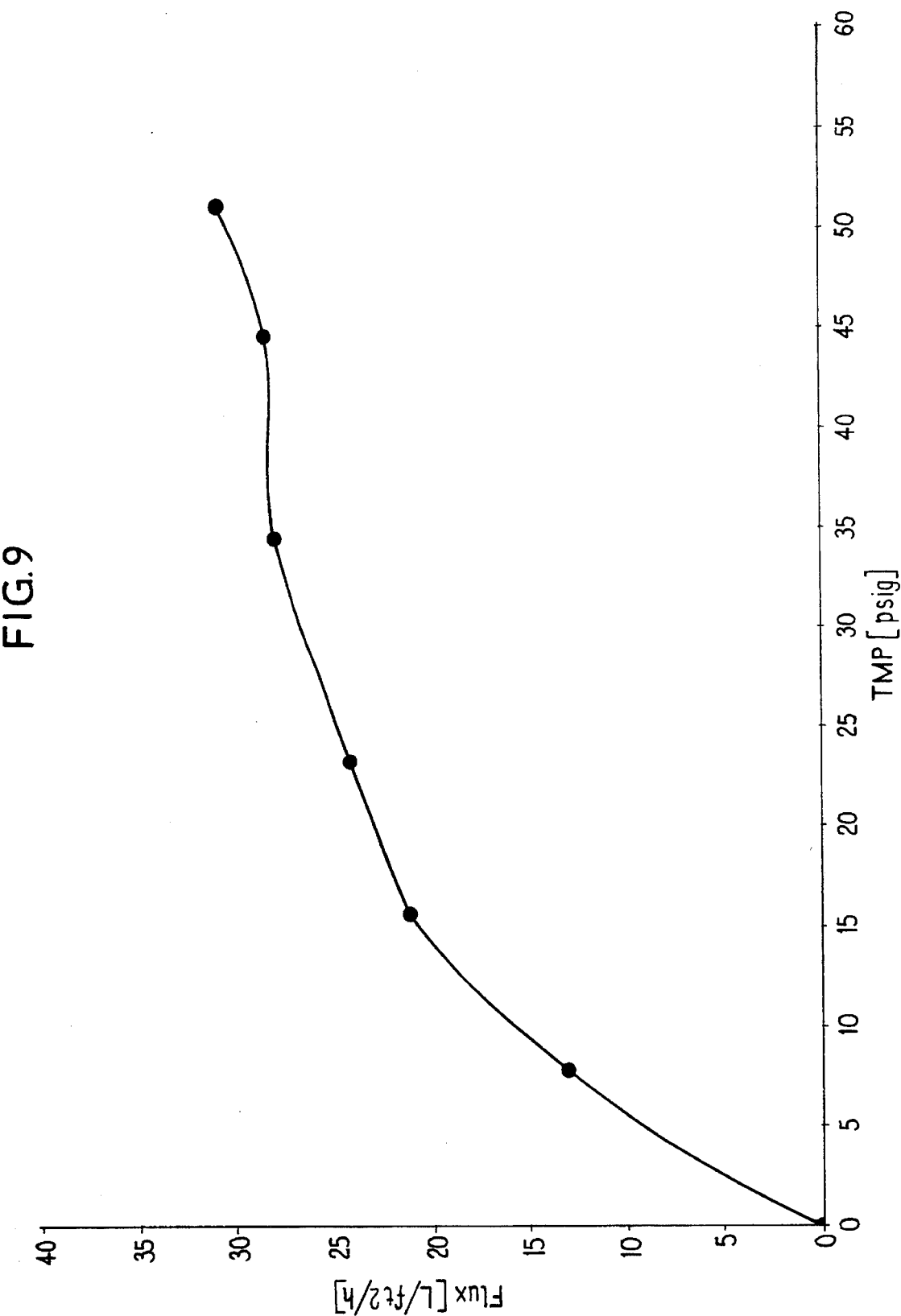
FIG. 9 is a graph of flux versus TMP for a short pathlength experimental TFF module using a 30 kDa regenerated cellulose membrane.
Figure 10:
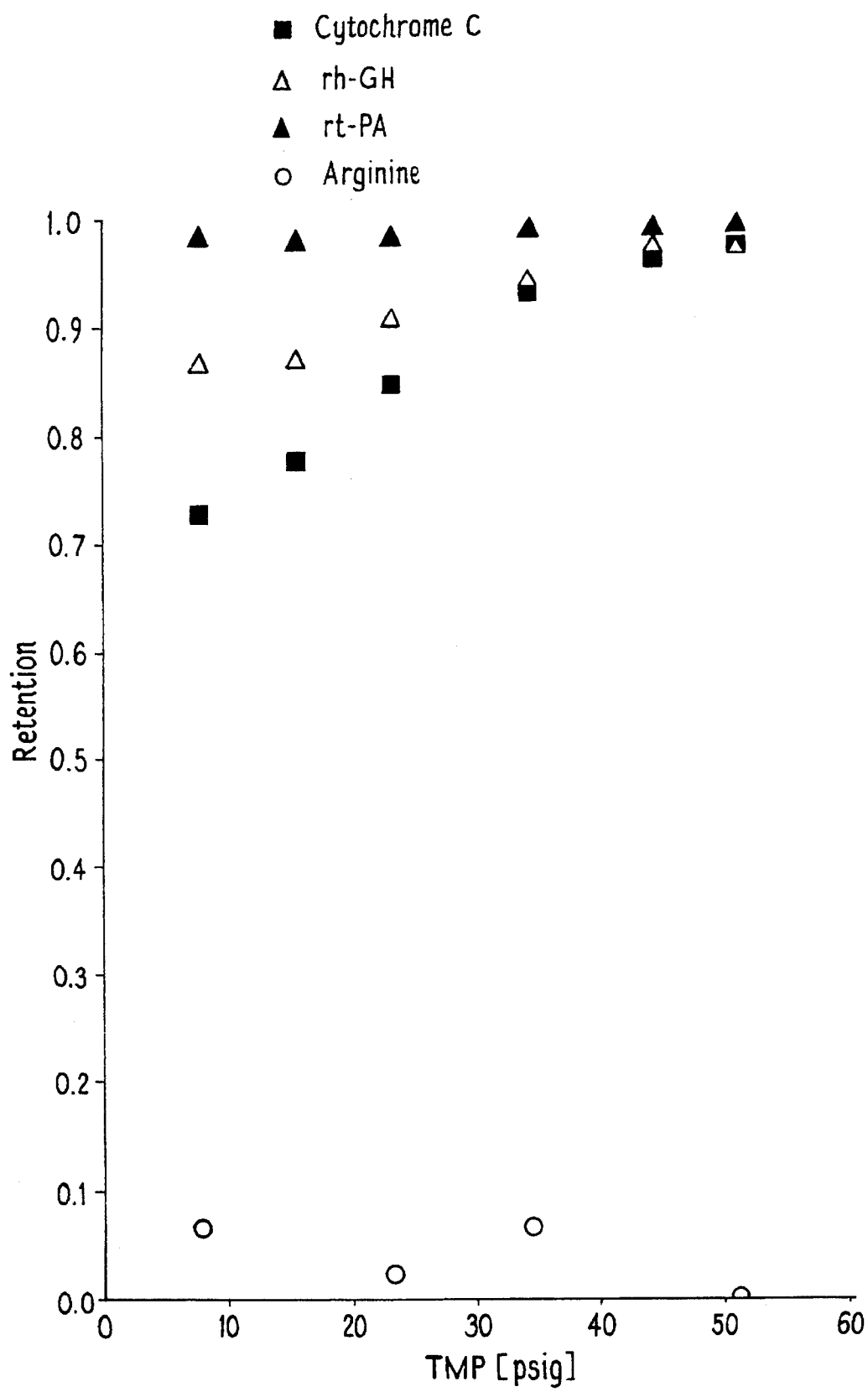
FIG. 10 is a graph of retention versus TMP for a mixture containing Cytochrome-C (squares), rh-GH (open triangles), rt-PA (solid triangles), and arginine (open circles).

FIG. 9 is the flux versus TMP curve, which shows a transition point at a TMP of approximately 24 psi. FIG. 10 shows retention versus TMP for the four species in the mixture and indicates that rt-PA is fully retained by the membrane, while arginine flows through freely at all TMPs. FIG. 10 also indicates that above a TMP of 24 psi (at the pressure-independent flux), Cytochrome-C, rh-GH and rt-PA are all highly retained. Below a TMP of 24 psi (at the pressure-dependent flux), however, the retention of these species is dependent on their molecular weight.

Figure 11:
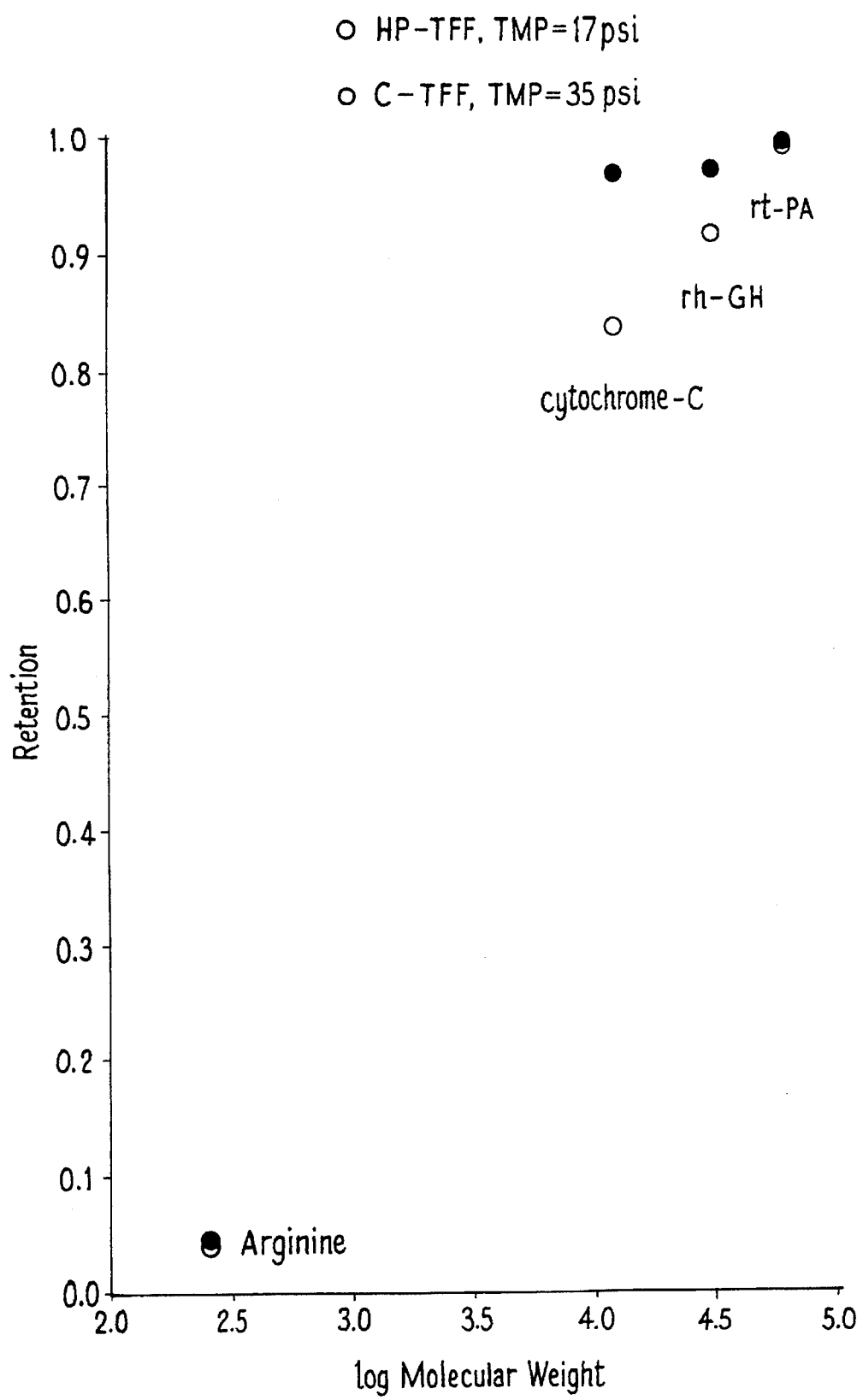
FIG. 11 is a graph of retention versus log molecular weight for a mixture containing Cytochrome-C, rh-GH, rt-PA, and arginine using C-TFF (solid circles) and HP-TFF (open circles).

FIG. 11 is a graph of retention versus log molecular weight for the four species in the mixture using HP-TFF (open circles) and C-TFF (solid circles). FIG. 11 shows that Cytochrome-C, rh-GH, and rt-PA are all highly retained in the C-TFF mode, providing little or no separation of these proteins. In the HP-TFF mode, however, separation of these proteins can be obtained based on molecular weight differences.

It is noted that for all the examples herein the ultrafiltration rate generally decreased.

The process and apparatus herein may also be employed for separating cell debris from whole cells. In continuous perfusion cultures, it would be desirable not only to exchange media components and remove products, but also to remove cell debris that would otherwise accumulate during the run. While this can be accomplished by adding a purge stream, such a stream will remove both debris and whole cells. The device herein would be employed with a membrane having a pore size close to the size of the whole cells, i.e., a microporous membrane. It is expected that this invention could be used to obtain better size separation in microfiltration processes analogous to the ultrafiltration processes shown in the examples above.

The scope of the invention is not to be construed as limited by the illustrative embodiments set forth herein, but is to be determined in accordance with the appended claims. Variations within the scope of the invention may be made by those ordinarily skilled in the art without departing from the essence of the invention as claimed herein.

What is claimed is:

1. A process for separating species of interest having a molecular weight of about 1 to 1000 kDa from a mixture, which process comprises filtering the mixture by tangential-flow filtration through a filtration membrane having a pore size that separates said species of interest from the mixture, while maintaining flux at a level ranging from about 5 to 100% of transition point flux in the pressure-dependent region of the flux versus TMP curve, whereby the species of interest are selectively separated from the mixture, and wherein transmembrane pressure decreases or remains approximately constant as the filtration progresses.

2. The process of claim 1 wherein the flux is from about 50 to 100% of the transition point flux.

3. The process of claim 1 wherein the flux is from about 75 to 100% of the transition point flux.

4. The process of claim 1 wherein the mixture is undiluted.

5. The process of claim 1 wherein retentate from the filtration is recycled to a tank containing the mixture to be separated and the process is repeated.

6. The process of claim 1 wherein transmembrane pressure decreases as the filtration progresses.

7. The process of claim 1 wherein transmembrane pressure remains approximately constant as the filtration progresses.

8. The process of claim 1 wherein the species of interest are biological entities selected from the group consisting of proteins, polypeptides, amino acids, colloids, mycoplasm, endotoxins, viruses, carbohydrates, RNA, and DNA.

9. The process of claim 8 wherein the species of interest are proteins or polypeptides.

10. The process of claim 1 wherein the species of interest are less than ten times larger or smaller in molecular weight than the other species of interest of the mixture.

11. The process of claim 1 wherein transmembrane pressure is held substantially constant along the membrane at a level no greater than the transmembrane pressure at the transition point of the filtration.

12. A process for separating at least two proteins or polypeptides from each other that are contained in a mixture, wherein the proteins or polypeptides differ from each other in molecular weight by less than ten fold, which process comprises filtering the mixture by tangential-flow filtration through a filtration membrane having a pore size that separates the polypeptides or proteins from the mixture, while maintaining flux at a level ranging from about 5 to 100% of transition point flux in the pressure-dependent region of the flux versus TMP curve, whereby the proteins or polypeptides are selectively separated from the mixture, and wherein transmembrane pressure decreases or remains approximately constant as the filtration progresses.

* * * * *